US008598106B2

(12) United States Patent
Schwarz et al.

(10) Patent No.: US 8,598,106 B2
(45) Date of Patent: Dec. 3, 2013

(54) ANTI-MICROBIAL COMPOSITION EXHIBITING RESIDUAL ANTI-MICROBIAL PROPERTIES ON A SURFACE

(75) Inventors: Ulrich Schwarz, Manchester (GB); Stephen Brian Falder, Manchester (GB); John Yates, Manchester (GB)

(73) Assignee: Byotrol PLC, Greater Manchester (GB)

( * ) Notice: Subject to any disclaimer, the term of this patent is extended or adjusted under 35 U.S.C. 154(b) by 0 days.

(21) Appl. No.: 13/176,213

(22) Filed: Jul. 5, 2011

(65) Prior Publication Data

US 2011/0263665 A1 Oct. 27, 2011

Related U.S. Application Data

(63) Continuation of application No. 12/678,668, filed as application No. PCT/GB2008/003149 on Sep. 17, 2008, now Pat. No. 8,003,593.

(30) Foreign Application Priority Data

Sep. 17, 2007 (GB) ................................... 0718114.2
Jul. 17, 2008 (GB) ................................... 0813098.1

(51) Int. Cl.
*C11D 3/48* (2006.01)
*C11D 1/62* (2006.01)
*C11D 9/36* (2006.01)

(52) U.S. Cl.
USPC ........... 510/384; 510/235; 510/237; 510/238; 510/391; 510/421; 510/422; 510/466; 510/490; 510/503; 510/504

(58) Field of Classification Search
USPC ......... 510/235, 237, 238, 384, 391, 421, 422, 510/466, 490, 503, 504
See application file for complete search history.

(56) References Cited

U.S. PATENT DOCUMENTS

| | | | |
|---|---|---|---|
| 3,970,755 A | 7/1976 | Gazzard et al. | |
| 4,173,643 A | 11/1979 | Law | |
| 4,540,505 A | 9/1985 | Frazier | |
| 4,637,890 A | 1/1987 | Crabtree et al. | |
| 4,698,148 A | 10/1987 | Keane | |
| 4,718,941 A | 1/1988 | Halverson et al. | |
| 4,767,547 A | 8/1988 | Straathof et al. | |
| 4,788,176 A | 11/1988 | Wieserman et al. | |
| 4,902,349 A | 2/1990 | Wakizaka et al. | |
| 4,933,096 A | 6/1990 | Demeyere et al. | |
| 4,954,335 A * | 9/1990 | Janchipraponvej | 424/70.28 |
| 5,178,495 A | 1/1993 | Cameron | |
| 5,196,029 A | 3/1993 | Kawase et al. | |
| 5,244,666 A | 9/1993 | Murley | |
| 5,405,542 A | 4/1995 | Trinh et al. | |
| 5,529,690 A | 6/1996 | Pashley et al. | |
| 5,538,667 A | 7/1996 | Hill et al. | |
| 5,591,708 A | 1/1997 | Richter | |
| 5,645,841 A | 7/1997 | Hill et al. | |
| 5,651,959 A | 7/1997 | Hill et al. | |
| 5,665,374 A | 9/1997 | Hill et al. | |
| 5,670,055 A | 9/1997 | Yu et al. | |
| 5,681,637 A | 10/1997 | Kessler et al. | |
| 5,688,449 A | 11/1997 | Fox | |
| 5,711,936 A | 1/1998 | Hill et al. | |
| 5,730,967 A | 3/1998 | Hill et al. | |
| 5,733,529 A | 3/1998 | Hill et al. | |
| 5,733,536 A | 3/1998 | Hill et al. | |
| 5,753,214 A * | 5/1998 | Yoshioka et al. | 424/70.2 |
| 5,830,447 A * | 11/1998 | Hutchins et al. | 424/70.12 |
| 5,834,114 A | 11/1998 | Economy et al. | |
| 5,856,245 A | 1/1999 | Caldwell et al. | |
| 5,869,071 A | 2/1999 | Wieselman et al. | |
| 5,869,172 A | 2/1999 | Caldwell | |
| 5,874,164 A | 2/1999 | Caldwell | |
| 5,888,488 A | 3/1999 | Fukuchi | |
| 5,955,093 A | 9/1999 | Woo et al. | |
| 6,013,683 A * | 1/2000 | Hill et al. | 516/67 |
| 6,030,936 A | 2/2000 | Lu et al. | |
| 6,039,965 A | 3/2000 | Dolan et al. | |
| 6,080,706 A | 6/2000 | Blanvalet et al. | |
| 6,107,268 A | 8/2000 | Yahiaoui et al. | |
| 6,121,224 A | 9/2000 | Fonsny et al. | |
| 6,177,399 B1 | 1/2001 | Mel et al. | |
| 6,645,480 B2 | 11/2003 | Giles | |
| 6,656,923 B1 | 12/2003 | Trinh et al. | |
| 6,806,248 B2 | 10/2004 | Grainger et al. | |
| 6,821,042 B2 | 11/2004 | Baker et al. | |

(Continued)

FOREIGN PATENT DOCUMENTS

CA 1087955 A1 10/1980
CA 1087955 ABS A1 10/1980

(Continued)

OTHER PUBLICATIONS

Abstract of Japanese Patent JP9175904 entitled Improved Water-Based Suspended Agrochemical Composition, published Aug. 7, 1997.
Abstract of Japanese Patent JP4065409A2 entitled Surface-Modifying Agent for Polymeric Material Curable With Actinic Energy Ray and Production Thereof issued Mar. 2, 1992.
Abstract of Japanese Patent JP4110329A2 entitled Surface Modifier for Active Energy Ray-Curable Polymer Material and Preparation Thereof issued Apr. 10, 1992.

(Continued)

*Primary Examiner* — Charles Boyer
(74) *Attorney, Agent, or Firm* — Nelson Mullens Riley & Scarborough LLP

(57) ABSTRACT

The present invention describes a formulation comprising: (A) at least one surfactant; and (B) an anti-microbial composition that comprises (i) an anti-microbial agent with surfactant properties; (ii) a hydrophobic material and (iii) a polar solvent.

25 Claims, No Drawings

(56) References Cited

U.S. PATENT DOCUMENTS

| | | | |
|---|---|---|---|
| 6,821,943 | B2 | 11/2004 | Avery et al. |
| 6,846,846 | B2 | 1/2005 | Modak et al. |
| 7,060,666 | B2 | 6/2006 | McHattie et al. |
| 7,674,473 | B2 | 3/2010 | Falder et al. |
| 7,713,520 | B2 | 5/2010 | Sakuta |
| 7,745,425 | B2 | 6/2010 | Modak et al. |
| 7,875,673 | B2 | 1/2011 | Gee et al. |
| 8,003,593 | B2 | 8/2011 | Schwarz et al. |
| 8,178,484 | B2* | 5/2012 | Schwarz et al. ............ 510/384 |
| 2003/0031687 | A1* | 2/2003 | Falder et al. ................. 424/400 |
| 2006/0018847 | A1* | 1/2006 | Kroepke et al. ............... 424/59 |
| 2007/0196291 | A1* | 8/2007 | Sakuta ........................... 424/59 |
| 2008/0027172 | A1* | 1/2008 | Gee et al. ..................... 524/837 |
| 2008/0131389 | A1* | 6/2008 | Shibuya et al. .............. 424/70.5 |
| 2009/0069436 | A1* | 3/2009 | MacGregor ................... 514/635 |
| 2012/0071525 | A1* | 3/2012 | Schwarz et al. ............. 514/372 |

FOREIGN PATENT DOCUMENTS

| | | |
|---|---|---|
| DE | 3739711 A1 | 8/1989 |
| EP | 0 181 182 A2 | 5/1986 |
| EP | 0 206 028 A1 | 12/1986 |
| EP | 0 233 954 A2 | 9/1987 |
| EP | 0 340 938 A1 | 11/1989 |
| EP | 0 513 637 A2 | 11/1992 |
| EP | 1076088 A1 | 2/2001 |
| EP | 1266652 A1 | 12/2002 |
| GB | 991597 A | 5/1965 |
| GB | 2102288 A | 2/1983 |
| GB | 2 247 171 A | 2/1992 |
| GB | 2346375 A | 8/2000 |
| GB | 2374011 A | 10/2002 |
| JP | 07-179890 A | 7/1995 |
| JP | 10-195032 | 7/1998 |
| JP | 11-286405 | 10/1999 |
| JP | 2000119690 A | 4/2000 |
| JP | 2000198999 A | 7/2000 |
| JP | 2004532300 A | 10/2004 |
| JP | 2006-188468 | 7/2006 |
| JP | 2009512611 A | 3/2009 |
| JP | 2010533691 A | 10/2010 |
| JP | 59-74197 A | 4/2013 |
| WO | 91/07090 A1 | 5/1991 |
| WO | 92/21320 A1 | 12/1992 |
| WO | 93/10209 A1 | 5/1993 |
| WO | 96/39249 A1 | 12/1996 |
| WO | 98/35933 A1 | 8/1998 |
| WO | 9962493 A1 | 12/1999 |
| WO | 00/00024 A1 | 1/2000 |
| WO | 0100777 A1 | 1/2001 |
| WO | 0121755 A1 | 3/2001 |
| WO | 01/64034 A1 | 9/2001 |
| WO | 02062142 A1 | 8/2002 |
| WO | WO2007078412 A1 | 7/2007 |
| WO | 2009010749 A2 | 1/2009 |
| WO | 2009037445 A1 | 3/2009 |

OTHER PUBLICATIONS

Abstract of Japanese Patent JP57179522A2 entitled Deodorizing Filer for Air Conditioner issued Nov. 5, 1982.
Abstract of Japanese Patent JP7252177A2 entitled Surface Modifier and Method for Surface Modification Using the Same issued Oct. 3, 1995.
Abstract of Japanese Patent JP7292289A2 entitled Antibacterial Floor Coating Material and Coated Floor Surface issued Nov. 7, 1995.
Abstract of Japanese Patent JP9256217A2 entitled Polytetrafluoroethylene Fiber and Its Production issued Sep. 30, 1997.
Abstract of Japanese Patent JP10016158A2 entitled Antibacterial Biaxially Oriented Polypropylene Film issued Jan. 20, 1998.
Abstract of Japanese Patent JP10095468A2 entitled Container Made of Antibacterial Material issued Apr. 14, 1998.
Abstract of Japanese Patent JP10095469A2 entitled Storage Container for Medical Instrument and Medical Material issued Apr. 14, 1998.
Abstract of JP10095935A2 entitled Antimicrobial Interior Material issued Apr. 14, 1998.
Abstract of JP10152396A2 entitled Material Having Crystalline Oriented Membrane of Titanium Dioxide and Its Production issued Jun. 9, 1998.
Article published in PNAS May 22, 2001, vol. 98, No. 11, pp. 5981-5985 by Joerg C. Tiller, et al., entitled Designing surfaces that kill bacteria on contact.
Patents Directorate, United Kingdom Intellectual Property Office, Combined Search and Examination Report under Sections 17 and 18(3), Jan. 19, 2009, United Kingdom Application No. GB0817024.3, Applicant Byotrol PLC.
Patents Directorate, United Kingdom Intellectual Property Office Examination Report under Section 18(3), Apr. 9, 2010, United Kingdom Application No. GB0817024.3, Applicant Byotrol PLC.
PCT Notification of Transmittal of the International Search Report and the Written Opinion of the ISA/European Patent Office, mailed Mar. 5, 2009, dated of actual completion of the International Search Feb. 27, 2009, International Application No. PCT/GB2008/003149, International Filing date Sep. 17, 2008, Applicant Byotrol PLC.
Colloid from Wilkipedia, the free encyclopedia, http://en.wilipedia.org/wilki/Colloid, Mar. 16, 2010.
PCT International Search Report, ISA/European Patent Office, mailed Jan, 29, 2009, actual completion of the International Search Jan. 20, 2009, date of publication of the International Search Report Apr. 2, 2009, International Application No. PCT/GB2008/002436, International Filing date Jul. 17, 2008, Applicant Byotrol PLC.
Abstract of JP 7179890(A), Jul. 18, 1995, Olympus Optical Co—espacenet—Bibliographic data.
United Kingdom Patents Directorate, Intellectual Property Office, Official Action: Patents Act 1977: Examination Report under Section 18(3), issued Oct. 22, 2010, GB Patent Application No. 0817024.3, Reference BYOCX/P41725GB.
United Kingdom Patents Directorate, Intellectual Property Office, Official Action: Patents Rules 2007 Notification of Grant: Patent Serial No. GB2453038, issued on Feb. 8, 2011, GB Patent Application No. 0817024.3, Reference BYOCX/P41725GB.
Federal Ministry of Commerce & Industry, Trade Marks, Patents & Designs Division, Patents Branch, Federal Secretariat, Garki, Abjua, Nigeria, Acceptance of Patent Notification, issued Jun. 15, 2010, on NG Patent Application No. NG/C/2010/304.
United States Patent and Trademark Office, Non-Final Office Action, mailed Dec. 1, 2011, U.S. Appl. No. 12/669,415, filed Apr. 14, 2010, Ulrich Schwarz.
United States Patent and Trademark Office, Non-Final Office Action, mailed Jan. 4, 2012, U.S. Appl. No. 13/281,707, filed Oct. 26, 2011, Ulrich Schwarz.
Akzo Nobel, Product Information, Surfactants, ARQUAD 16-29 Hexadecyltrimethylanmmonium chloride INCI Name Cetrimonlum Chloride CAS No. 112-02-7, ARQUAD is a registered trademark in many countries. Version: 0.2 Issued: Nov. 6, 2008. http://www.surfactants.akzonobel.com.
Kenya Industrial Property Institute, Substantive Examination (Section 44 and Regulation 28), date of invitation Jul. 7, 2011, Kenya Patent Application No. KE/P/2010/001059, filed Sep. 17, 2008, Applicant—Byotrol PLC.
State Intellectual Property Office of the People's Republic of China, First Office Action (PCT application entering into the national phase), date of issue Dec. 2, 2011, Chinese Patent Application No. 200880116123.4, Applicant—Byotrol PLC.
State Intellectual Property Office of the People's Republic of China, First Office Action (PCT application entering into the national phase), date of issue Mar. 30, 2011, Chinese Patent Application No. 200880107233.4, Applicant—Byotrol PLC.
United States Patent and Trademark Office, Supplemental Notice of Allowability, mailed Jul. 15, 2011, U.S. Appl. No. 12/678,668, filed Jun. 30, 2012, First Named Inventor—Ulrich Schwarz.
United States Patent and Trademark Office, Issue Notification, U.S. Appl. No. 12/678,668, filed Jun. 30, 2012 First Named Inventor—Ulrich Schwarz.

(56) References Cited

OTHER PUBLICATIONS

United States Patent and Trademark Office, Non-Final Office Action, mailed Dec. 1, 2011, U.S. Appl. No. 12/669,415, filed Apr. 14, 2010, First Named Inventor—Ulrich Schwarz.

United States Patent and Trademark Office, Notice of Allowance and Fee(s) Due, mailed Feb. 15, 2012, U.S. Appl. No, 12/669,415, filed Apr. 14, 2010, Ulrich Schwarz et al.

United States Patent and Trademark Office, Issue Notification, U.S. Appl. No. 12/669,415, filed Apr. 14, 2010, Ulrich Schwarz et al.

Response to Office Action, filed Apr. 4, 2012 with the U.S. Patent and Trademark Office, in response to the outstanding Office Action, mailed Jan. 4, 2012, U.S. Appl. No. 13/281,707, filed Oct. 26, 2011, Ulrich Schwarz et al.

Supplemental Response to Office Action, filed May 2, 2012, to the Response filed Apr. 4, 2012, with the U.S. Patent and Trademark Office, in response to the outstanding Office Action, mailed Jan. 4, 2012, U.S. Appl. No. 13/281,707, filed Oct. 26, 2011, Ulrich Schwarz et al.

Response to Office Action, filed Feb. 7, 2012, with the U.S. Patent and Trademark Office, in response to the outstanding Office Action, mailed Dec. 1, 2011, U.S. Appl. No. 12/669,415, filed Apr. 14, 2010, Ulrich Schwarz et al.

Kenya Industrial Property Institute, Certificate of Grant of a Patent, KE 487 granted Jan. 6, 2012, Kenya Patent Application No. KE/P/2010/001059, filed Sep. 17, 2008, Byotrol PLC of Riverside Works, Collyhurst Road, Manchester M40 7RU, United Kingdom.

Mexican Institute of Industrial Property, Notice of Patent Grant for Mexican Patent No. 297322, issue date Mar. 22, 2012, Byotrol PLC.

English translation of an official action issued by Mexican Patent and Trademark Office, issued Oct. 12, 2012, Mexican Patent Application No, MX/A/2010/000694, filed Sep. 17, 2008, Byotrol PLC.

State Intellectual Property Office of the People's Republic of China, Second Office Action (PCT application entering into the national phase), date of issue Apr. 1, 2012, Chinese Patent Application No. 200880107233.4, Applicant—Byotrol PLC.

United States Patent and Trademark Office, Final Office Action, mailed Jul. 11, 2012, U.S. Appl. No. 13/281,707, filed Oct. 26, 2011, Ulrich Schwarz.

PCT International Search Report, ISA/European Patent Office, mailed Jan. 29, 2009, actual completion of the International Search Jan. 20, 2009, date of publication of the International Search Report Apr. 2, 2009, International Application No. PCT/GB2008/002436, International Filing date Jul. 17, 2008, Applicant Byotrol PLC.

English translation of an official action issued by the State Intellectual Property Office of the People's Republic of China, issued Oct. 19, 2012, Chinese Patent Application No. 200880116123.4, filed Sep. 17, 2008, byotrol PLC.

English translation of an official action issued by Mexican Patent and Trademark Office, issued Oct. 12, 2012, Mexican Patent Application No. MX/A/2010/000694, filed Sep. 17, 2008, Byotrol PLC.

Official Action Date Jan. 4, 2013 for Australian Patent Application No. 2008300404.

Official Action and Translation Dated Jan. 22, 2013 for Japanese Patent Application No. 2010-516568.

Official Action for U.S. Appl. No. 13/281,707 Dated Jan. 2, 2013.

Official Action for AU 2008277406 Dated Nov. 9, 2012.

Official Action for EP 08775967.6 Dated Jan. 8, 2013.

Notice of Allowance (and English Translation Thereof) for CN200880107233.4 Dated Dec. 5, 2012.

\* cited by examiner

ANTI-MICROBIAL COMPOSITION EXHIBITING RESIDUAL ANTI-MICROBIAL PROPERTIES ON A SURFACE

CROSS REFERENCE TO RELATED APPLICATIONS

This application is a Continuation Application of U.S. application Ser. No. 12/678,668, filed Jun. 30, 2010, which is the national phase, under 35 U.S.C. §371, of International Application No.: PCT/GB2008/003149 filed Sep. 17, 2008, which designated the United States of America and which claimed priority to Great Britain Application No. GB 0718114.2 filed Sep. 17, 2007 and Great Britain Application No. GB 0813098.1 filed Jul. 17, 2008. The present application claims the benefit of priority to and incorporates herein by reference, in their entireties, the disclosures of U.S. application Ser. No. 12/678,668, International Application No.: PCT/GB2008/003149, and Great Britain Application Nos. GB 0718114.2 and 0813098.1.

This invention relates to formulations comprising anti-microbial compositions. In particular, the present invention relates to formulations for use in cleaning processes which comprise an anti-microbial composition.

A typical cleaning process has a number of features including the removal of visible soilage and stains and is usually performed using aqueous solutions of one or more of soaps/detergents/surfactants and oxidising agents. These systems solubilise the soilage, including fatty/greasy deposits and soluble materials that constitute "dirt". However, a significant failing of these systems is that they typically do not fully eliminate the organic and inorganic materials that are contaminating or dirtying the surface, usually only reducing the amount to being not highly visible to the naked eye, these residues can be more than sufficient to act as nutrients for micro-organisms that cause nuisance, damage, unpleasant odours, health risk and/or spoilage to the surfaces/articles that have been cleaned. In some situations micro-organisms can even be introduced onto the surfaces/articles being cleaned from the water used in the cleaning process itself.

Micro-organisms are known to present health hazards due to infection or contamination. They can also cause spoilage of items such as clothing and unpleasant odours. When micro-organisms are present on the surface of a substrate they can replicate rapidly to form colonies. The microbial colonies form a coating on the substrate surface, which is known as a biofilm. Biofilms frequently consist of a number of different species of micro-organisms which in turn can be more difficult to eradicate than individual microorganisms.

Micro-organisms attach themselves to substrates forming a biofilm comprising a "calyx" of polysaccharides and/or similar natural polymers as the affixing mechanism. Without this affixing point, the reproduction of the micro-organism particularly bacteria cannot proceed, or is at least seriously impaired.

Biofilms form when micro-organisms such as bacteria adhere to surfaces in aqueous environments and begin to excrete Extra cellular secretion, a slimy, glue-like substance that can anchor them to all kinds of materials such as metals, plastics, soil particles, medical implant materials and tissue. A biofilm can be formed by a single bacterial species but more often biofilms consist of several species of bacteria, as well as fungi, algae, protozoa, debris and corrosion products. Essentially, bacterial biofilms may form on any surface exposed to bacteria and some amount of water. Once anchored to a surface, biofilm microorganisms carry out a variety of detrimental or beneficial reactions (by human standards), depending on the surrounding environmental conditions.

Many anti-microbial agents that can destroy microorganisms which are present in a wide range of environments such as medical, industrial, commercial, domestic and marine environments are known. Many of the known anti-microbial agents have previously been included in compositions for use in various applications and environments.

The known anti-microbial agents and compositions that contain these anti-microbial agents destroy micro-organisms by a number of different mechanisms.

For example, many anti-microbial agents are poisonous to micro-organisms and, therefore, destroy micro-organisms with which they are contacted. Examples of this type of anti-microbial agent include hypochlorites (bleaches), phenol and compounds thereof, arsenene and salts of copper, tin and arsenic. However, some of these agents can be highly toxic to humans and animals as well as to micro-organisms. Consequently these anti-microbial agents are dangerous to handle, and specialist handling, treatment and equipment are therefore required in order to handle them safely. The manufacture and disposal of compositions comprising this type of anti-microbial agent can, therefore, be problematic. There can also be problems associated with the use of compositions containing this type of anti-microbial agent, particularly in consumer materials where it is difficult to ensure that they are used for designated purposes.

Herein, unless the context indicates otherwise, "toxicity" is intended to refer to toxicity to complex organisms such as mammals. References to "toxic" are to be construed accordingly.

Once the anti-microbial agents enter the environment they can affect the health of life forms that they were not intended to affect. Furthermore, the anti-microbial agents are often highly stable and can cause environmental problems for long periods of time.

Other known anti-microbial agents that are commonly used include organic and inorganic salts of heavy metals such as silver, copper or tin. These salts produce toxic rinsates, which can cause problems to the environment. For example, the rinsates of such salts are poisonous to aquatic life. Again, once the toxic compounds enter the environment they are not easily broken down and can cause persistent problems.

Other anti-microbial agents currently in use include antibiotic type compounds. Antibiotics disrupt the biochemistry within microorganisms, for example by selectively diluting solutions to destroy or inhibit the growth of harmful microorganisms. Although antibiotics are effective, it is currently believed that they may selectively permit the development of resistant strains of the species that they are used against. These resistant strains are then able to reproduce unimpeded by the use of known antibiotics. Thus, there is a growing concern that wide and uncontrolled use of antibiotic materials in the wider environment, as opposed to their controlled use in medical contexts, could produce significant long-term risks.

Another method of microbial control is the use of oxidising agents in materials, such as household bleach, which can be based on hypochlorite or peroxides such as hydrogen peroxide. These materials are effective in a wet environment for sterilization and cleansing. However, the materials do not provide long-term passive anti-microbial control and sanitisation. By "passive control" we mean that the substrate counters microbial infection on its own by some property within it even in a dry environment, so that it does not require a cleaning regime to be effective at controlling micro-organisms.

Another method involves the use of materials such as quaternary ammonium compounds that act as lytic (bursting) agents for the microbial cells. This method has the disadvantage of not being effective against all strains of micro-organism so that resilient colonies can develop that have a high degree of "survivability" to disinfection with quaternary ammonium compounds so that they need to be alternated in use. Additionally, these materials are highly water soluble so easily wash away or can easily contaminate moist materials in contact with them.

The listing or discussion of an apparently prior-published document in this specification should not necessarily be taken as an acknowledgement that the document is part of the state of the art or is common general knowledge.

There is a need to provide formulations for a variety of applications and uses, particularly cleaning applications that have anti-microbial properties and that address one or more of the problems set out above. However, it is not a straight forward matter to do this. There are regulations such as the Biocidal Products Directive (Directive 98/8/EC) which regulates the use of anti-microbial agents both in terms of the nature and the amount of a given anti-microbial agent that may be used. Additionally, the potential reactivity of an anti-microbial agent once in a formulation is important as some anti-microbial agents are rendered inactive by chemical reaction. Even where an anti-microbial agent is not deactivated by chemical reaction it may have its activity suppressed by other components of the formulation.

The present inventors have surprisingly found that the foregoing deficiencies can be overcome by the inclusion of certain anti-microbial compositions in formulations to which it is desired to provide anti-microbial properties. It has also been found that formulations prepared in this manner have some surprising and unexpected properties.

In particular, the present invention provides formulations comprising an anti-microbial composition suitable for a variety of consumer applications. The formulations that are within the scope of the present invention are surfactant containing formulations, for example surfactant based formulations. These surfactant containing formulations; for example surfactant based formulations, may comprise at least one non-ionic, anionic, cationic and/or amphoteric surfactant. In a particular aspect of the invention the formulation comprises at least one non-ionic and/or amphoteric surfactant.

Examples of the formulations of the invention include, but are not limited to, surface cleaners such as those intended for use in bathrooms, kitchens, living areas, hard floor cleaners, carpet cleaners, furniture cleaners, glass/mirror cleaners; toilet care products including solid toilet cleaners such as rim devices and those designed to be placed in the cistern, liquid toilet cleaners excluding those comprising hypochlorite bleaches; dishwashing products such as washing up liquids and preparations from dishwashing machines such as dishwashing solids (eg powders and tablets) & liquids; laundry products such as solid detergents (eg powders and tablets), liquid detergents and fabric conditioners and "2 in 1" products comprising detergent and fabric conditioner; cleaning products intended for use outdoors such as those for cleaning for wood, stone, concrete or plastics, for example patio cleaner, garden furniture cleaners/treatments, BBQ cleaners, wall and fence cleaners/treatments, plant sprays such as those intended to remove insects such as aphides from plants; food sprays, such as those suitable for use in food preservation; personal care products such as bath and shower products; soaps, including liquid and solid soaps, hand sanitisers, deodorants and antiperspirants, haircare products including shampoos, for example anti-scalp odour shampoos, shampoos for the control of head lice eggs and anti-dandruff shampoos, hair conditioners, hair styling products such as hair mousses, gels and sprays, skin care products such as shaving products, cosmetics and products for hair removal; baby products including baby cleaning and cleansing products such as baby bath, soaps, wipes, moisturisers, nappy rash cream, products for cleaning surfaces that have regular & high incidence of infant & baby contact; first aid products and products for treating ailments and illnesses, including products for the topical treatment and/or prevention of minor infections such as athletes foot, spot/acne prevention/treatment products; foot hygiene products, including those for use on the foot and those for the treatment/deodourisation of foot ware, particularly sports foot wear; products for cleaning and/or deodourising vehicles such as cars.

The formulations of the invention comprise an anti-microbial composition that comprises (i) an anti-microbial agent with surfactant properties; (ii) a hydrophobic material and (iii) a polar solvent.

More particularly, the formulations of the invention comprise (A) at least one surfactant (referred to hereinafter as component (A) or the at least one formulation surfactant) and (B) an anti-microbial composition that comprises (i) an anti-microbial agent with surfactant properties; (ii) a hydrophobic material and (iii) a polar solvent.

The formulation surfactant (A) may be any suitable surfactant or combination of surfactants, for example at least one non-ionic, anionic, cationic and/or amphoteric surfactant. In a particular aspect of the invention the formulation surfactant (A) comprises at least one non-ionic and/or amphoteric surfactant. The selection of the formulation surfactants (A) will depend on the nature of and the intended purpose of the formulation. Suitable surfactants for use in formulations intended for different purposes will be within the knowledge of the person of ordinary skill in the art.

The pH of the formulations of the invention can vary within wide limits. Typically, the pH of a formulation of the invention will be similar to that of known formulations which are intended to be used for the same purpose or a similar purpose to a given formulation of the invention. For example, a formulation that is intended to come into contact with the skin or the hair, such as a hand wash formulation or a shampoo formulation or other personal care or first aid formulations as listed above will typically have a pH which is not irritate the skin, for example from about pH 5 to about pH 8, such as from about pH 5.5 to about pH 7.5. On the other hand formulations for use for purposes such as kitchen or bathroom cleaning may have a low pH, such as a pH of 3 or below, for example about 2.

In one preferred group of formulations of the invention the formulation surfactant (A) comprises at least one non-ionic surfactant. For example the formulation surfactant (A) may consist essentially of at least one non-ionic surfactant or the formulation surfactant (A) may consist of at least one non-ionic surfactant. If the formulation surfactant (A) consists of at least one non-ionic surfactant it will not contain other types of surfactants, for example it will be free of amphoteric surfactants, anionic surfactants and cationic surfactants. Examples of non-ionic surfactants that can be used in these formulations are listed below.

In another preferred group of formulations of the invention the formulation surfactant (A) is an amphoteric surfactant. Amphoteric surfactants can be used alone or in combination with a non-ionic surfactant. If a combination of an amphoteric surfactant and a non-ionic surfactant is used the weight ratio of the two types of surfactant can vary within wide limits, for example from 1% of amphoteric surfactant to 99% of nonionic surfactant to 99% of amphoteric surfactant to 1% of non-ionic surfactant, based on the total weight of the formulation surfactant (A). Preferably the amphoteric surfactant and the non-ionic surfactant are used in approximately equal amounts by weight.

In one aspect of the invention, preferred formulations comprise up to about 5% by weight (based on the total weight of the formulation) amphoteric surfactant, although higher levels of amphoteric surfactant can be used in some formulations. As an example, the present invention provides formulations having a pH of from about 5 to about 8, more preferably from about 5.5 to about 7.5 and comprising an amphoteric surfactant and a non-ionic surfactant, wherein the amphoteric surfactant is present in an amount of up to about 5% by weight (based on the total weight of the formulation). In such formulations, the total amount of surfactant is not particularly limited and the total amount of surfactant may be an amount that is typical in the art for the particular type of formulation in question. Examples of preferred formulations comprising an amphoteric surfactant and a non-ionic surfactant have a total surfactant content of about 10% by weight, wherein no more that 5% by weight (based on the total weight of the formulation) is amphoteric surfactant.

Suitable cationic surfactants for use as the formulation surfactant (A) include but are not limited to distearyl dimethyl ammonium chloride, lauryl trimethyl ammonium chloride, alkyl trimethyl ammonium methosulfate, coco trimethyl ammonium chloride and cetyl pyridinium chloride.

Suitable non-ionic surfactants for use as the formulation surfactant (A) include but are not limited to ethylene oxide/propylene oxide block polymers, polyethoxylated sorbitan esters, fatty esters of sorbitan, ethoxylated fatty esters (containing from 1 to 25 units of ethylene oxide), polyethoxylated $C_8$-$C_{22}$ alcohols (containing from 1 to 25 units of ethylene oxide), polyethyoxylated $C_6$-$C_{22}$ alkylphenols (containing from 5 to 25 units of ethylene oxide), alkylpolyglycosides. Examples include but are not limited to nonyl phenol ethoxylate (9EO), Nonyl phenol ethoxylate (2EO), octyl phenol ethoxylate (10EO), $C_{12}$/$C_{14}$ synthetic ethoxylate (8EO), stearyl alcohol ethoxylate (7EO), cetostearyl alcohol ethoxylate (20EO), coconut fatty amine ethoxylate (10EO), sorbitan monolaurate ethoxylate, 80% PO/20% EO, coconut diethanolamide (shampoo foam booster), sorbitan monolaurate, sorbitan monolaurate 4EO, di-isopropyl adipate, alkyl poly glucosides, such as $C_{6-20}$, preferably $C_{8-10}$ alkyl glucosides, eg Surfac APG (D-Glucopyranose oligomers $C_{8-10}$ alkyl glucosides, CAS 161074-97-1, available from Seppic, UK), and cetostearyl stearate. Other suitable non-ionic surfactants include Neodol 25-7 (C12/15 alcohol 7 ethoxylate (EO), CAS 68131-39-5), Surfac LM90/85 (C12/15 alcohol 9 ethoxylate (EO), CAS 68131-39-5), Surfac 65/95 (C9/11 alcohol 6.5 ethoxylate (EO), CAS 68439-45-2), Tomadol PF9 (C9/11 alcohol 6.0 ethoxylate (EO), CAS 68439-46-3), Surfac T80 Veg (Polysorbate 80, Polyoxyethylene sorbate mono oleate, CAS 9005-65-6), Tween 60 (Polysorbate 60, Polyoxyethylene sorbate mono stearate, CAS 9005-67-8), Tween 40 (Polysorbate 40, Polyoxyethylene sorbate mono palmitate, CAS 9005-66-7), Surfac T-20 (Polysorbate 20, Polyoxyethylene sorbate mono laurate, CAS 9005-64-5), Surfac PGHC (Hydrogenated Castor oil 40EO, CAS 61788-85-0), Ninol 49-CE (Coconut diethanolamide, CAS 68603-42-9).

Suitable amphoteric surfactants for use as the formulation surfactant (A) include but are not limited to $C_6$-$C_{20}$ alkylamphoacetates or amphodiacetates (such as cocoamphoacetates), $C_{10}$-$C_{18}$ alkyldimethyl betaines, $C_{10}$-$C_{18}$ alkyl amidopropyldimethyl betaines. Examples include but are not limited to coconut amphoteric surfactant cocoamidopropyl betaine (CAPB) (Surfac B4, CAS 61789-40-9), coco imidazoline betaine, oleo amido propyl betaine, and tall oil imidazoline. A particularly preferred amphoteric surfactant is cocoamidopropyl betaine.

Other suitable surfactants include those that exhibit non-ionic or cationic type properties at pHs below about 8, for example between about pH 5 and about pH 7 or 8. It will be appreciated that the behaviour of such surfactants depends on factors such as their pKa and which surfactants are suitable for use in a given formulation will depend on the pH of the formulations. Examples of surfactants which exhibit properties that can vary with pH and that can be used in the formulations of the invention include but are not limited to amine oxides such as those having an average carbon chain length of from 8 to 20, eg 12 or 14 such as $C_{10}$-$C_{18}$ alkyldimethyl amine oxides and $C_8$-$C_{22}$ alkoxyethyldihydroxyethylamine oxides, for example dimethyl laurylamine oxide (eg Surfac AO30 from Surfachem and manufactured by Stepan as Ammonyx LO), alkyl ether carboxylates and alkyl ether phosphates, such as those having an average chain length of from 8 to 12, eg 12 or 14 (eg Laureth 11 carboxylic acid, sold by Univar as Akypo RLM 100 and Laureth 4 phosphate, sold by Surfachem and manufactured by Schill and Seilacher as Silaphos MDE 124). These surfactants can be used in combination with other surfactants such as non-ionic surfactants.

Preferred combinations of surfactants include but are not limited to CAPB and a non-ionic surfactant, such as APG, an amine oxide and a non-ionic surfactant, such as APG.

It will be appreciated that the formulations of the invention can comprise other ingredients commonly used in the art. The nature of any other ingredients used will depend on the nature and intended purpose of the formulation. For example, the additional ingredients used in a bath/shower product are likely to be different to those used in a toilet care product which will be different again from those used in a dishwashing or laundry product. The person of ordinary skill in the art will know which additional ingredients are suitable for use in formulations for different applications. Additional ingredients that may be used in the formulations of the invention include but are not limited to water, antioxidants, thickeners, corrosion inhibitors, foam makers and breakers, abrasives, chelating agents such as tetrasodium EDTA, sodium chloride, acids such as citric acid, colorants, fragrances, emollients and hair and/or skin rejuvenating and/or protecting agents.

For the avoidance of doubt, when we state herein that the formulations comprise a surfactant or is surfactant based we mean that the formulations comprise a surfactant in addition to the surfactant(s) present in the anti-microbial compositions used in those formulations.

It will be appreciated that the amount of formulation surfactant (A) in the formulations of the invention will depend on factors such as the intended purpose of the formulation. Typically, the formulations of the invention comprise from 1 to 30% by weight of formulation surfactant (A), preferably from 2 to 25% by weight. For household cleaning products the amount of surfactant (A) is typically from about 2 to 10% by weight. For dishwashing products the amount of surfactant (A) is typically from about 10 to 25% by weight, for example from about 15 to 20% by weight. For personal care products the amount of surfactant (A) is typically from about 10 to 20% by weight for example from 15 to 20% by weight. It will be appreciated that these percentages are examples only and that some products may comprise surfactant (A) in an amount outside the range specified for a given product type.

By the term "anti-microbial" we mean that a compound or composition that kills and/or inhibits the growth of microbes (micro-organisms). The term "microbiocidal" is used to refer to compounds or compositions that kill microbes. The compositions used in the invention are anti-microbial and/or microbiocidal.

A micro-organism or microbe is an organism that is microscopic (too small to be seen by the human eye). Examples of micro-organisms include bacteria, fungi, yeasts, moulds, mycobacteria, algae spores, archaea and protists. Micro-organisms are generally single-celled, or unicellular organisms. However, as used herein, the term "micro-organisms" also include viruses.

Preferably, the compositions used in the formulations of the invention comprise at least one anti-microbial agent selected from anti-bacterial, anti-fungal, anti-algal, anti-sporal, anti-viral, anti-yeastal and anti-moldal agents and mixtures thereof. More preferably, the compositions of the invention comprise at least one anti-bacterial, anti-fungal and/or anti-moldal agent.

As used herein, the terms anti-bacterial, anti-fungal, anti-algal, anti-viral, anti-yeastal and anti-moldal agents are intended to refer to agents which inhibit the growth of the respective microorganisms but do not necessarily kill the microorganisms and agents which kill the respective microorganisms. Thus, for example, within the term anti-bacterial we include agents which inhibit the growth of bacteria but may not necessarily kill bacteria and bactericidal agents which do kill bacteria.

As the skilled person will appreciate, the word ending "cidal" as used in for example "bactericidal" and "fungicidal" is used to describe agents which kill the microorganism to which it refers. Thus in these examples, bactericidal refers to an agent that kills bacteria and fungicidal refers to an agent that kills fungus. Examples of bactericides include myobactericides and tuberculocides. Preferably, the compositions of the invention comprise at least one agent selected from bactericidal, fungicidal, algicidal, sporicidal, virucidal, yeasticidal and moldicidal agents and mixtures thereof. More preferably, the compositions of the invention comprise at least one bactericidal, virucidal, fungicidal and/or moldicidal agent.

The compositions used in the formulations of the invention are effective against a wide range of organisms, including Gram negative and Gram positive spore formers, yeasts, viruses.

By way of example, the micro-organisms which the compositions used in the present invention can be effective against include:

Viruses such as HIV-1 (AIDS Virus), Hepatatis B Virus (HVB), Hepatitis C Virus (HCV), Adenovirus, Herpes Simplex, Influenza, Respiratory Syncytial Virus (RSV), Vaccinia, Avian Influenza virus, Avian Bronchitis, Pseudorabies virus, Canine Distemper, Newcastle Disease, Rubella, Avian Polyomavirus, Feline leukemia, Feleine picornavirus, Infectious Bovine rhinotracheitis, Infectious Bronchitis (Avian IBV), Rabies, Transmissible gastroenteritis virus, Marek's Disease;

Funguses such as *Trichophyton mentagrophytes, Aspergillus niger, Candida albicans, Aspergillus flavus, Aspergillus fumigatus, Trichophyton interdigitale, Alternaria tenius, Fusarium oxysporum, Geotrichum candidum, Penicillium digitatum, Phytophthora infestans, Rhizopus nigricans, Trichoderma harzianum, Trichophyton interdigitale,* Bacteria such as *Pseudomonas aeruginosa, Staphylococcus aureus, Salmonella choleraesuis, Acinetobacter baumannii, Brevibacterium ammoniagenes, Campylobacter jejuni, Enterobacter aerogenes, Escherichia coli, Klebsiella pneumoniae, Proteus mirabilis, Pseudomonas cepacia, Salmonella schottmuelleri, Salmonella typhi, Salmonella typhimurium, Serratia marcescens, Shigella dysenteriae, Shigella flexneri, Shigella sonnei, Staphyloccus epidermidis, Streptoccus faecalis, Streptoccus faecalis* (Vancomycin resistant), *Streptococcus pyogenes, Vibrio chlorae, Xanthomonas axonopodis* pv *citri* (Citrus canker), *Acinetobacter calcoaceticus, Bordetella bronchiseptica, Chlamydia psittaci, Enterobacter cloacae, Enterococcus faecalis, Fusobacterium necrophorum, Legionella pneumophila, Listeria monocytogenes, Pasteurella multocida, Proteus vulgaris, Salmonella enteritidis, Mycoplasma gallisepticum, Yersinia enterocolitica, Aeromonas salmonicida, Pseudomonas putida, Vibrio anguillarum.*

In particular, the compositions used in the invention are effective against *P. aeruginosa* (ATCC 15442, PaFH72/a), *E. coli* (ATCC 10536, ECFH64/a, 0157:H7 (toxin producing strain), CCFRA/896, 0157:H7 (non-toxigenic strain), CCFAA/6896, ATCC 10538), *S. aureus* (including MRSA, (e.g. NCTC 12493 MRSA, ATCC 12493 MRSA), VISA, ATCC 6538, 5a FH73/a), *Entercoccus hirea* (ATCC 10541, EhFH 65/a), Feline Coronavirus (SARS surrogate), Feline Calcivirus (Hum. *Norovirus* surrogate), *Salmonella typhimurium* (StFH 68/b), *Yersinia enterocolitica* (YE FH67/b), *Listeria monocytogenes* (Lm FH66/c), *Saccharomyces cerevisiae, Bacillus Subtilis* (ATCC 6633), *Bacillus stearothermophilus* (NCTC 10339), *clostridium dificile* (NCTC 11209), *Candida albicans* (ATCC 1023), *Aspergillus niger* (ATCC 16404), *Mycobacterium smegmatis* (TB stimulant).

By the term "anti-microbial agent with surfactant properties" (component (i)) we mean a material which can kill or inhibit the growth of microbes (micro-organisms) and also has the effect of altering the interfacial tension of water and other liquids or solids and/or reduces the surface tension of a solvent in which it is used. More particularly, the anti-microbial agents with surfactant properties used in the present invention can kill or inhibit the growth of microbes and typically when introduced into water lower the surface tension of water.

A class of compounds that is particularly suitable for use as the anti-microbial agent with surfactant properties in the present invention is the class of compounds known as quaternary ammonium compounds, also know as "quats". These compounds typically comprise at least one quaternary ammonium cation with an appropriate anion. The quaternary ammonium cations are permanently charged, independent of the pH of their solution.

The structure of the cation can be represented as follows:

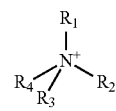

The groups $R_1$, $R_2$, $R_3$ and $R_4$ can vary within wide limits and examples of quaternary ammonium compounds that have anti-microbial properties will be well known to the person of ordinary skill in the art.

Each group $R_1$, $R_2$, $R_3$ and $R_4$ may, for example, independently be a substituted or unsubstituted and/or straight chain or branched and/or interrupted or uninterrupted alkyl, aryl, alkylaryl, arylalkyl, cycloalkyl, (aromatic or non-aromatic) heterocyclyl or alkenyl group. Alternatively, two or more of $R_1$, $R_2$, $R_3$ and $R_4$ may together with the nitrogen atom form a substituted or unsubstituted heterocyclic ring. The total number of carbon atoms in the groups $R_1$, $R_2$, $R_3$ and $R_4$ must be at least 4. Typically the sum of the carbon atoms in the groups $R_1$, $R_2$, $R_3$ and $R_4$ is 10 or more. In a preferred aspect of the invention at least one of the groups $R_1$, $R_2$, $R_3$ and $R_4$ contains from 8 to 18 carbon atoms. For example, 1, 2, 3 or 4 of $R_1$, $R_2$, $R_3$ and $R_4$ can contain from 8 to 18 carbon atoms or 10 to 16 carbon atoms.

Suitable substituents for the groups $R_1$, $R_2$, $R_3$ and $R_4$ may be selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$C(=O)R', —O(CR'R")$_r$NR"C(=O)R', —O(CR'R")$_r$NR"SO$_2$R', —OC(=O)NR'R", —NR'C(=O)OR", —SO$_2$R', —SO$_2$NR'R", and —NR'SO$_2$R", where R' and R" are individually hydrogen, $C_1$-$C_8$alkyl, cycloalkyl, heterocyclyl, aryl, or arylalkyl, and r is an integer from 1 to 6, or R' and R" together form a cyclic functionality, wherein the term "substituted" as applied to alkyl, alkenyl, heterocyclyl, cycloalkyl, aryl, alkylaryl and arylalkyl refers to the substituents described above, starting with F and ending with —NR'SO$_2$R".

When one or more of $R_1$, $R_2$, $R_3$ and $R_4$ is interrupted, suitable interrupting groups include but are not limited to heteroatoms such as oxygen, nitrogen, sulphur, and phosphorus-containing moieties (e.g. phosphinate). A preferred interrupting group is oxygen.

Suitable anions for the quats include but are not limited to halide anions such as the chloride, fluoride, bromide or iodide and the non halide sulphonate.

Preferred quats are those having the formula:

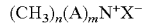

wherein A may be as defined above in relation to $R_1$, $R_2$, $R_3$ and $R_4$. $X^-$ is selected from chloride, fluoride, bromide or iodide and sulphonate (preferably chloride or bromide), n is from 1 to 3 (preferably 2 or 3) and m is from 1 to 3 (preferably 1 or 2) provided that the sum of n and m is 4. Preferably, A is a $C_{6-20}$ (e.g. $C_{8-18}$, i.e. having 8, 9, 10, 11, 12, 13, 14, 15, 16, 17 or 18 carbon atoms or $C_{8-12}$) substituted or unsubstituted and/or straight chain or branched and/or interrupted or uninterrupted alkyl, aryl, alkylaryl, arylalkyl or cycloalkyl group (wherein suitable substituents are as defined above in relation to $R_1$, $R_2$, $R_3$ and $R_4$). Each group A may be the same or different.

A preferred group of the compounds of formula $(CH_3)_n(A)_mN^+X^-$ are those wherein n=3 and m=1. In such compounds A may be as defined above and is preferably a $C_{6-20}$ substituted or unsubstituted and/or straight chain or branched and/or interrupted or uninterrupted alkyl, aryl, or alkylaryl group. Examples of this type of quaternary ammonium compound include Cetrimide (which is predominately trimethyltetradecylammonium bromide), dodecyltrimethylammonium bromide, trimethyltetradecylammonium bromide, hexadecyltrimethylammonium bromide.

Another preferred group of the compounds of formula $(CH_3)_n(A)_mN^+X^-$ are those wherein n=2 and m=2. In such compounds A may be as defined above in relation to $R_1$, $R_2$, $R_3$ and $R_4$. Preferably A is a $C_{6-20}$ substituted or unsubstituted and/or straight chain or branched and/or interrupted or uninterrupted alkyl, aryl, or alkylaryl group. For example, A may represent a straight chain, unsubstituted and uninterrupted $C_{8-12}$ alkyl group or a benzyl group. In these compounds, the groups A may be the same or different. Examples of this type of compound include didecyl dimethyl ammonium chloride and dioctyl dimethyl ammonium chloride.

Examples of the preferred quaternary ammonium compounds described above include the group of compounds which are generally called benzalkonium halides and aryl ring substituted derivatives thereof. Examples of compounds of this type include benzalkonium chloride, which has the structural formula:

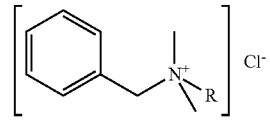

wherein R may be as defined above in relation to $R_1$, $R_2$, $R_3$ and $R_4$. Preferably, R is a $C_{8-18}$ alkyl group or the benzalkonium chloride is provided and/or used as a mixture of $C_{8-18}$ alkyl groups, particularly a mixture of straight chain, unsubstituted and uninterrupted alkyl groups n-$C_8H_{17}$ to n-$C_{18}H_{37}$, mainly n-$C_{12}H_{25}$ (dodecyl), n-$C_{14}H_{29}$ (tetradecyl), and n-$C_{16}H_{33}$ (hexadecyl).

Other preferred quaternary ammonium compounds include those in which the benzene ring is substituted, for example alkyldimethyl ethylbenzyl ammonium chloride. As an example, a mixture containing, for example, equal molar amounts of alkyl dimethyl benzyl ammonium chloride and alkyldimethyl ethylbenzyl ammonium chloride may be used.

Mixtures of, for example, one or more alkyl dimethyl benzyl ammonium chlorides and one or more compounds of formula $(CH_3)_2(A)_2N^+X^-$, such as didecyl dimethyl ammonium chloride may be used.

Typically, mixtures of quaternary ammonium compounds are used. In these mixtures, the quaternary ammonium compounds may be mixed with any suitable inert ingredients. Commercially available benzalkonium chloride often contains a mixture of compounds with different alkyl chain lengths. Examples of commercially available benzalkonium chlorides are shown in the following Table.

| CAS Number | Chemical Name |
|---|---|
| 61789-71-7 | Alkyl (61% C12, 23% C14, 11% C16, 2.5% C8 & C10, 2.5% C18) dimethyl benzyl ammonium chloride |
| | Alkyl (47% C12, 18% C14, 10% C18, 10% C16, 15% C8-C10) dimethylbenzyl ammonium chloride |
| | Alkyl (50% C12, 30% C14, 17% C16, 3% C18) dimethylbenzyl ammonium chloride |
| | Alkyl (50% C14, 40% C12, 10% C16) dimethylbenzyl ammonium chloride |
| 137951-75-8, 68989-01-5 | Alkyl (50% C14, 40% C12, 10% C16) dimethylbenzyl ammonium saccharinate |
| | Alkyl (58% C14, 28% C16, 14% C12) dimethylbenzyl ammonium chloride |

-continued

| CAS Number | Chemical Name |
|---|---|
| 68424-85-1 | Alkyl (60% C14, 25% C12, 15% C16) dimethylbenzyl ammonium chloride |
| | Alkyl (60% C14, 30% C16, 5% C12, 5% C18) dimethylbenzyl ammonium chloride |
| 68989-00-4 | Alkyl (61% C12, 23% C14, 11% C16, 3% C10, 2% C8) dimethylbenzyl ammonium chloride |
| | Alkyl (61% C12, 23% C14, 11% C16, 5% C18) dimethyl benzyl ammonium chloride |
| | Alkyl (61% C12, 23% C14, 11% C16, 5% C8, C10, C18) dimethylbenzyl ammonium chloride |
| | Alkyl (65% C12, 25% C14, 10% C16) dimethylbenzyl ammonium chloride |
| | Alkyl (67% C12, 25% C14, 7% C16, 1% C18) dimethylbenzyl ammonium chloride |
| | Alkyl (67% C12, 25% C14, 7% C16, 1% C8, C10, C18) dimethylbenzyl ammonium chloride |
| | Alkyl (90% C14, 5% C12, 5% C16) dimethylbenzyl ammonium chloride |
| | Alkyl (93% C14, 4% C12, 3% C16) dimethylbenzyl ammonium chloride |
| 68424-85-1 | Alkyl (95% C14, 3% C12, 2% C16) dimethyl benzyl ammonium chloride |
| | Alkyl (95% C14, 3% C12, 2% C16) dimethyl benzyl ammonium chloride dihydrate |
| | Alkyl (95% C14, 3% C12, 2% C16) dimethyl benzyl ammonium chloride monohydrate |
| | Alkyl (C14, C12, C16) dimethyl benzyl ammonium chloride |
| | Alkyl dimethyl cumenyl ammonium chloride |
| | Alkyl dimethyl isopropyl benzyl ammonium chloride |
| | Alkyl(68% C12, 32% C14)dimethyl dimethylbenzyl ammonium chloride |
| 71011-24-0 | Alkyl* dimethyl benzyl ammonium bentonite *(as in fatty acids of tallow) |
| 122-18-9 | Alkyl* dimethyl benzyl ammonium chloride *(100% C16) |
| 122-19-0 | Alkyl* dimethyl benzyl ammonium chloride *(100% C18) |
| 68424-85-1 | Alkyl* dimethyl benzyl ammonium chloride *(40% C12, 40% C14, 20% C16) |
| 68391-01-5 | Alkyl* dimethyl benzyl ammonium chloride *(41% C14, 28% C12, 19% C18, 12% C16) |
| | Alkyl* dimethyl benzyl ammonium chloride *(47% C12, 18% C14, 15% (C5-C15), 10% C18, 10% C16) |
| 8045-22-5, 8001-54-5 | Alkyl* dimethyl benzyl ammonium chloride *(50% C12, 30% C14, 17% C16, 3% C18) |
| 68391-01-5 | Alkyl* dimethyl benzyl ammonium chloride *(55% C16, 20% C14, 20% C12, 5% C18) |
| 68391-01-5 | Alkyl* dimethyl benzyl ammonium chloride *(55% C16, 27% C12, 16% C14, 2% C18) |
| | Alkyl* dimethyl benzyl ammonium chloride *(58% C14, 28% C16, 14% C12) |
| | Alkyl* dimethyl benzyl ammonium chloride *(60% C14, 25% C12, 15% C16) |
| 68424-85-1 | Alkyl* dimethyl benzyl ammonium chloride *(60% C14, 30% C16, 10% C12) |
| 53516-76-0 | Alkyl* dimethyl benzyl ammonium chloride *(60% C14, 30% C16, 5% C18, 5% C12) |
| 68391-01-5 | Alkyl* dimethyl benzyl ammonium chloride *(61% C12, 23% C14, 11% C16, 5% C18) |
| 68989-00-4 | Alkyl* dimethyl benzyl ammonium chloride *(61% C12, 23% C14, 11% C16, 3% C10, 2% C18) |
| | Alkyl* dimethyl benzyl ammonium chloride *(65% C12, 23% C14, 12% C16) |
| 68424-85-1 | Alkyl* dimethyl benzyl ammonium chloride *(65% C12, 25% C14, 10% C16) |
| 68391-01-5 | Alkyl* dimethyl benzyl ammonium chloride *(67% C12, 25% C14, 7% C16, 1% C18) |
| | Alkyl* dimethyl benzyl ammonium chloride *(67% C12, 25% C14, 7% C16, 1% C8, C10, and C18) |
| | Alkyl* dimethyl benzyl ammonium chloride *(67% C12, 27% C14, 6% C16) |
| | Alkyl* dimethyl benzyl ammonium chloride *(68% C12, 25% C14, 7% C16) |
| | Alkyl* dimethyl benzyl ammonium chloride *(90% C14, 5% C12, 5% C16) |
| 68424-85-1 | Alkyl* dimethyl benzyl ammonium chloride *(93% C14, 4% C12, 3% C16) |
| 68607-20-5 | Alkyl* dimethyl benzyl ammonium chloride *(95% C16, 5% C18) |
| | Alkyl* dimethyl benzyl ammonium chloride *(as in fatty acids of coconut oil) |

| CAS Number | Chemical Name |
|---|---|
| | Alkyl* dimethyl benzyl ammonium chloride *(C8-18) |
| | Alkyl* dimethyl benzyl ammonium dichloroisocyanurate *(60% C14, 30% C16, 6% C12, 4% C18) |
| | Alkyl* dimethyl benzyl ammonium ion alkyl** amine *(C12, C14, C16) **(C10, C12, C14, C16) |
| | Alkyl* dimethyl isopropylbenzyl ammonium chloride *(60% C14, 30% C16, 5% C12, 5% C18) |
| | Alkyl* dodecylbenzyl dimethyl ammonium chloride *(67% C18, 33% C16) |
| | Alkyldimethylbenzyl ammonium chloride |
| 55963-06-9 | BTC 2125-m |
| 73049-75-9 | Dialkyl* methyl benzyl ammonium chloride *(60% C14, 30% C16, 5% C18, 5% C12) |
| | Dimethyl benzyl hydrogenated tallow ammonium cation |
| 7281-04-1 | Dodecyl dimethyl benzyl ammonium bromide |
| 139-07-1 | Dodecyl dimethyl benzyl ammonium chloride |
| 87175-02-8 | Dodecylbenzyl alkyl (70% C12, 30% C14) dimethyl ammonium chloride |
| | N-Alkyl* dimethyl benzyl ammonium chloride *(57% C12, 18% C14, 8% C16, 6% C10-C18, 5% C8) |
| 139-08-2 | Tetradecyl dimethyl benzyl ammonium chloride |
| | Tetradecyl dimethyl benzyl ammonium chloride dihydrate |

It will be appreciated that a single CAS number often refers to more than one blend or mixture. A CAS classification for a commercial preparation typically covers blends comprising specified compounds in amounts within defined ranges. The compositions having the CAS numbers quoted above are only examples of compositions having a given CAS number that may be used in the present invention.

Suitable quaternary ammonium compounds in which $R^1$, $R^2$, $R^3$, $R^4$ are interrupted by a heteroatom include domiphen bromide ((Dodecyldimethyl-2-phenoxyethyl)ammonium bromide) and benzethonium chloride (benzyldimethyl[2-[2-[4-(1,1,3,3-tetramethylbutyl)phenoxy]ethoxy]ethyl]ammonium chloride).

Other quaternary ammonium compounds suitable for use in the invention include, but are not limited to, alkylpyridinium compounds, such as cetylpyridinium chloride, and bridged cyclic amino compounds such as the hexaminium compounds.

Other examples of quaternary ammonium compounds which may be used include Cetalkonium Chloride; Cetylpyridinium Chloride; Glycidyl Trimethyl Ammonium Chloride; Stearalkonium Chloride; Zephiran chloride (R); Hyamine 3500; Diisobutylphenoxyethoxyethyldimethylbenzylammonium chloride; Hyamine 1622(R); Cetalkonium Chloride; Cetyldimethylbenzylammonium chloride; Triton K 12; Cetyltrimethylammonium bromide; Retarder LA; 1-Hexadecylpyridinium chloride; Glycidyltrimethylammonium chloride; Benzethonium Chloride CAS 121-54-0; Cetalkonium Chloride CAS 122-18-9; Cetrimide CAS 8044-71-1; Cetylpyridinium Chloride (anhydrous) CAS 123-03-5; Stearalkonium Chloride CAS 122-19-0; and Cetrimonium Bromide CAS 57-09-0.

Particularly preferred quaternary ammonium compounds include benzyldimethyl-n-tetradecyl-ammonium chloride, benzyldimethyl-n-dodecyl-ammonium chloride, n-dodecyl-n-tetradecyldimethyl-ammonium chloride and benzyl-$C_{12}$-$C_{16}$-alkyl-dimethyl-ammonium chloride, benzyl-cocoalkyl-dimethyl-ammonium chloride, di-n-decyldimethylammonium chloride.

An example of a suitable mixture is a composition comprising octyl decyldimethyl ammonium chloride, didecyl dimethyl ammonium chloride, dioctyl dimethyl ammonium chloride, and alkyl ($C_{14}$, 50%; $C_{12}$, 40%, $C_{16}$, 10%) dimethyl benzyl ammonium chloride (in a ratio of about 2:1:1:2.67).

Another suitable mixture is a mixture of octyldecyl dimethyl ammonium chloride, didecyl dimethyl ammonium chloride, dioctyl dimethyl ammonium chloride, and alkyl ($C_{14}$, 50%, $C_{12}$, 40%, $C_{16}$, 10%) dimethyl benzyl chloride (in a ratio of about 2:1:1:2.67).

Another suitable mixture is octyl decyl dimethyl ammonium chloride, dioctyl dimethyl ammonium chloride, didecyl dimethyl ammonium chloride, and alkyl ($C_{14}$, 50%; $C_{12}$, 40%; $C_{16}$, 10%) dimethyl benzyl ammonium chloride (in a ratio of about 2:1:1:2.67).

Examples of other commercially available anti-microbial agents with surfactant properties include BAC 50 (from Thor biocides), and Nobac (Benzalkonium chloride, from Mason Quats).

The anti-microbial agents with surfactant properties that are used in the present invention are not limited to quaternary ammonium compounds. Any suitable anti-microbial agent with surfactant properties may be used.

Other anti-microbial agents with surfactant properties can include anionic and cationic surfactant materials as well as amphoteric materials. Examples include quaternary bisammonium surfactants, alkyl betaines, alkyl amine oxides, arginine-based cationic surfactants, anionic amino acid based surfactants and mixtures thereof, for example a mixture of alkyl betaine(s) and alkyl amine oxides.

An example of a Betaine which is suitable for use in the present invention is Macat® Ultra (available from Mason Chemical Company). Macat® Ultra CG comprises 30% coco ($C_{12}$) amidopropyl dimethyl glycine (betaine) in water.

An example of an alkyl amine oxide which is suitable for use in the present invention is Macat® Ultra CDO (available from Mason Chemical Company), a 30% solution of coco ($C_{12}$) amidopropyl dimethyl amine oxide in water.

One or more of any of the anti-microbial agents with surfactant properties described above may be used as component (i) in the compositions used in the invention.

The amount of component (i) in the compositions that are used in the present invention will vary depending on a number of factors, such as the intended use of the formulation in which the composition is used and the particular compound(s) used as component (i).

Preferable the component (i) comprises at least one quaternary ammonium compound. Combinations of quaternary ammonium compounds can be used. Combinations of one or more quaternary ammonium compounds and one or more other surfactants with surfactant properties can be used.

Compounds suitable for use as the hydrophobic material (component (ii)) include silanes, siloxanes, silicones, polysiloxanes, fluorine-containing aliphatic compounds and mixtures thereof. These hydrophobic materials can be used in combination with other materials such as polyalkylene glycols.

The hydrophobic material is typically chemically inert. The hydrophobic material is typically capable of associating with other components of the fluid by non-covalent bonds.

As used herein, the term "fluorine-containing aliphatic compounds" refers to $C_8$ to $C_{20}$ linear or branched alkanes or alkenes which contain at least 0.1 fluorine atoms per carbon atom and as a maximum are fully fluorinated. Typically, the fluorine-containing aliphatic compound will contain an average of from 1 to 2 fluorine atoms per carbon atom.

The hydrophobic material may for example comprise at least one polysiloxane, preferably at least one polydimethylsiloxane. For example, a mixture of two or more polysiloxanes having different molecular weights and/or viscosities may be used. When a mixture of polysiloxanes is used, the mixture preferably comprises at least one polysiloxane containing up to about 500, more preferably 50 to 200 (e.g. about 100) monomer units and at least one polysiloxane containing more than 500, more preferably 750 to 1000 monomer units. These polysiloxane typically has a viscosity of from 35 to 750 centistokes, preferably 35 to 400 centistokes, more preferably 35 to 150 centistokes, for example about 100 centistokes.

These polysiloxanes typically have a surface tension of less than 20 mN/m at 20° C., for example from 5 to 19 mN/m, more preferably from 7 to 14 mN/m and most preferably from 8 to 12 mN/m at 20° C. (eg about 10 mN/m at 20° C.).

Other hydrophobic materials that may be included in the compositions used in the present invention include shorter chain siloxane selected from those having the formulae $(H_3C)[SiO(CH_3)_2]_nSi(CH_3)_3$, and $(H_3C)[SiO(CH_3)H]_nSi(CH_3)_3$, and mixtures thereof, where n is an integer, of from 1 to 24, more preferably from 1 to 12 and most preferably from 1 to 8, for example n may be 1, 2, 3, 4, 5, 6, 7, 8, 9, 10, 11 or 12, especially 1, 2, 3 or 4. These materials are often referred to as (poly)dimethylsiloxanes (CAS # 9016-00-6) and (poly)methylhydrosiloxanes respectively. These materials are typically liquid at ambient temperature and pressure (e.g. about 20° C. at atmospheric pressure).

These siloxanes typically have a molecular weight of from about 100 to about 2000 g/mol, preferably from about 148 to about 1864 (such as from about 162 to about 1864 or about 148 to about 1528), more preferably from about 148 to about 976 (e.g. from about 162 to about 976 or about 148 to about 808), such as from about 148 to about 680 (e.g. from about 162 to about 680 or about 148 to about 568), particularly from about 148 to about 384 (e.g. from about 162 to about 384 or about 148 to about 328).

Examples of preferred (poly)dimethylsiloxanes are hexamethyldisiloxane (CAS # 107-46-0), octamethyltrisiloxane (CAS # 107-51-7), decamethyltetrasiloxane (CAS # 141-62-8), dodecamethylpentasiloxane (CAS # 141-63-9). These (poly)dimethylsiloxanes correspond to the compounds of formula $(H_3C)[SiO(CH_3)_2]_nSi(CH_3)_3$, wherein n=1, 2, 3 and 4 respectively.

The shorter chain siloxanes typically have a viscosity of from 0.1 to 100 centistokes, preferably from 0.2 to 20. Preferred siloxanes have a viscosity of from 0.5 to 5 centistokes, e.g. 0.65, 1, 1.5, 2, 3, 4, 5, 6, 7, 8, 9, or 10 centistokes.

The shorter chain siloxanes, due to their relatively low molecular weight, are relatively volatile. For example, they typically have a boiling point of less than about 120° C. at atmospheric pressure, for example from about 100 to 120° C. Hexamethyldisiloxane, for example, has a boiling point of about 101° C. at atmospheric pressure.

The component (ii) is generally also strongly hydrophobic. By this we include the meaning that it is repelled from a mass of water and by itself is substantially insoluble in water. By the term "substantially insoluble in water", we mean that the material typically has a solubility of less than 2 g/100 g water at 20° C. and atmospheric pressure, such as less than 1 g/100 g water, preferably, less than 0.5 g/100 g water, for example less than 0.1 g/100 g water, e.g. less than 0.01 g/100 g water.

The materials described above as suitable for use as component (ii) may be used alone or in combination. In particular, mixtures of siloxanes and/or polysiloxanes of different molecular weight may be used. Many commercially available siloxanes/polysiloxanes are provided as mixtures and these can be used without the need to separate the components of the mixture. Details of commercially available siloxanes which are suitable for use in the compositions of the invention are set out, for example, at http://www.clearcoproducts.com/standard_pure_silicones.html.

For example a mixture of two, three, four, five or more siloxanes may be used. If a combination of siloxanes is used the materials may be used in equal or differing amounts. For example each siloxane may be used in equimolar amounts or the amount by weight of each siloxane may be the same. Other suitable ratios (in terms of molar amounts or by weight of the total amount of siloxanes) when a mixture of two siloxanes are used range from 0.1:99.9 to 99.9:0.1, preferably from 1:99 to 99:1, more preferably from 95:5 to 5:95, for example from 10:90 to 90:10 or from 25:75 to 75:25. For example, if a combination of hexamethyldisiloxane and octamethyltrisiloxane is used any ratio described above may be used. One particular combination comprises hexamethyldisiloxane:octamethyltrisiloxane in a ratio of 95:5.

It is a preferred aspect of the invention to use a mixture of two or more siloxanes or polysiloxanes. The use of the combination of hexamethyldisiloxane and octamethyltrisiloxane is preferred as is the use of a shorter chain siloxane such as one or both of these materials together with one or more of polysiloxanes of higher molecular weight described above.

The anti-microbial compositions used in the invention comprise a polar solvent, component (iii). Suitable polar solvents include, but are not limited to, water, alcohols, esters, hydroxy and glycol esters, polyols and ketones, and mixtures thereof.

Suitable alcohols include, but are not limited to, straight or branched chain $C_1$ to $C_5$ alcohols, such as methanol, ethanol, n-propanol, iso-propanol, mixtures of propanol isomers, n-butanol, sec-butanol, tert-butanol, iso-butanol, mixtures of butanol isomers 2-methyl-1-butanol, n-pentanol, mixtures of pentanol isomers and amyl alcohol (mixture of isomers), and mixtures thereof.

Suitable esters include, but are not limited to, methyl acetate, ethyl acetate, n-propyl acetate, iso-propyl acetate, n-butyl acetate, iso-butyl acetate, sec-butyl acetate, amyl acetate (mixture of isomers), methylamyl acetate, 2-ethylhexyl acetate and iso-butyl isobutyrate, and mixtures thereof.

Suitable hydroxy and glycol esters include, but are not limited to, methyl glycol acetate, ethyl glycol acetate, butyl glycol acetate, ethyl diglycol acetate, butyl diglycol acetate, ethyl lactate, n-butyl lactate, 3-methoxy-n-butyl acetate, ethylene glycol diacetate, polysolvan O, 2-methylpropanoic acid-2,2,4-trimethyl-3-hydroxypentyl ester, methyl glycol, ethyl glycol, iso-propyl glycol, 3-methoxybutanol, butyl glycol, iso-butyl glycol, methyl diglycol, ethyl diglycol, butyl diglycol, iso-butyl diglycol, diethylene glycol, dipropylene glycol, ethylene glycol monohexyl ether and diethylene glycol monohexyl ether, and mixtures thereof.

Suitable polyols include, but are not limited to, ethylene glycol, propylene glycol, 1,3-butylene glycol, 1,4-butylene glycol, hexylene glycol, diethylene glycol, triethylene glycol and dipropylene glycol, and mixtures thereof.

Suitable ketones include, but are not limited to iso-butyl heptyl ketone, cyclohexanone, methyl cyclohexanone, methyl iso-butenyl ketone, pent-oxone, acetyl acetone, diacetone alcohol, iso-phorone, methyl butyl ketone, ethyl propyl ketone, methyl iso-butyl ketone, methyl amyl ketone, methyl iso-amyl ketone, ethyl butyl ketone, ethyl amyl ketone, methyl hexyl ketone, diisopropyl ketone, diisobutyl ketone, acetone, methyl ethyl ketone, methyl propyl ketone and diethyl ketone, and mixtures thereof.

Preferred polar solvents for use in the anti-microbial compositions include, but are not limited to, water, ethanol, n-propanol, isopropanol, diethylene glycol and dipropylene glycol and mixtures thereof. It is particularly preferred that the composition comprises water or a mixture of water and one or more alcohols selected from the alcohols described above. In such mixtures, water is preferably the major component.

The anti-microbial compositions may contain components in addition to components (i), (ii) and (iii) set out above. For example, one or more additional antimicrobial agents (iv) may be included. Any suitable additional antimicrobial agent(s) may be used, such as those described in the EPA (United States Environmental Protection Agency) Listing and Annex I of the EC Biocides Directive.

Suitable additional anti-microbial agents (iv) include amphoteric compounds, iodophores, phenolic compounds, and nitrogen based heterocyclic compounds.

Preferably, the additional antimicrobial agent(s) are water soluble at room temperature and pressure.

Examples of additional antimicrobial agents (iv) include polymeric biguanidines (e.g. polyhexamethylene biguanidine (PHMB)), isothiazalones, ortho phenyl phenol (OPP), and nitro bromopropanes (e.g. bronopol (INN), 2-bromo-2-nitropropane-1,3-diol) and polymerised quaternary ammonium compounds. In one aspect of the invention the anti-microbial composition (B) does not comprise any isothiazalones.

Particularly preferred additional antimicrobial agents (iv) include polymeric biguanidines. A particularly preferred additional antimicrobial agent (iv) is polyhexamethylene biguanidine (PHMB). PHMB is commercially available from Arch Biocides as Vantocil.

Preferred anti-microbial compositions (B) for use in the present invention include those comprising one or more quaternary ammonium compounds and at least on polymeric biguanidine such as PHMB. For example, the anti-microbial composition (B) may contain one or more quaternary ammonium compounds and at least one polymeric biguanidine such as PHMB as the only anti-microbial active agents.

The anti-microbial compositions that are used in the invention are typically made by a process which comprises the steps of (I) mixing component (i) and component (ii); (II) adding the polar solvent to the mixture formed in step (I); and (III) agitating the resulting mixture until a clear solution is formed.

If component (i) is a solid, step (I) can be carried out in sufficient polar solvent to dissolve component (i). Alternatively, some materials which may be used a component (i) are commercially available in solution. In this case, these materials can be used in step (I) in their commercially available form.

Typically, the mixture used in step (I) comprises from about 1 to about 25% by weight of a polar solvent, more preferably from about 2 to about 8% by weight polar solvent. If the amount of solvent used in step (I) is too great, the colloids will not form. The person of ordinary skill in the art could readily determine an appropriate amount of solvent to use. If too much solvent is used the initial cloudy solution will not become clear (the clear solution being associated with the formation of colloids). The polar solvent typically use in step (I) is water, although other polar solvents may be used alternatively or additionally.

If one or more additional antimicrobial agents (iv) are used, these may be introduced in step (I) or they may be added in step (II). If they are added in step (I) at least some of the additional antimicrobial agent may be included in the colloidal particles. If the additional antimicrobial agent(s) are added in step (II) they are more likely to simply dissolve in the polar solvent (provided of course that they are soluble in that solvent). However, they may also attach to the outer surface of the colloid.

Typically, the process to produce the compositions is carried out at room temperature with stirring. In step (I) the mixture is initially cloudy because the component (ii) is insoluble in the polar solvent.

Typically step (I) is complete when the solution becomes clear. It is thought that this clear solution contains colloids or micelles of the components (i) and (ii) and the additional anti-microbial agents (iv), if used.

If an antimicrobial agent that is not soluble in the polar solvent is used, it should be added in step (I) so that it may form part of the colloids.

In step (I) the components may be mixed in any manner suitable to maximize the formation of colloidal structures (e.g. micelles and vesicles). This may be achieved by slow addition of a component (i) to component (ii) or visa versa and then mixing (for example stirring overnight). The rate of addition of the components often needs to be regulated to prevent "shock" which can prevent colloid formation. It would be a routine matter for the person of ordinary skill in the art to determine a suitable rate of addition. The mixing/blending steps can also use techniques ultrasonic mixing/blending.

The compositions may be prepared in a concentration form (i.e. with little or no polar solvent) and diluted with polar solvent (e.g. water) when used.

It is believed that in the compositions used in the invention the majority (greater than 50% preferably greater than 75%, more preferably greater than 90% and most preferably substantially all (at least 97%) or 100%) of the component (i) and the component (ii) are present in colloids containing both of these components. If an additional anti-microbial agent is used, this material may also be contained in the colloids and/or may be dissolved in the polar solvent.

A colloid or colloidal dispersion is a heterogeneous mixture that visually appears to be a homogeneous solution. Some colloids are translucent because of the Tyndall effect, which is the scattering of light by particles in the colloid. Other colloids may be opaque or have a slight color. The colloids in the compositions of the present invention are typically not opaque.

In a colloid, the dispersed phase is made of tiny particles or droplets that are distributed evenly throughout the continuous phase. The size of the dispersed phase particles or droplets is typically between one nanometer and one micrometer. Heterogeneous mixtures with a dispersed phase in this size range may be called colloidal sols, colloidal emulsions, colloidal foams, colloidal suspensions or colloidal dispersions.

The dispersed phase particles or droplets are largely affected by the surface chemistry present in the colloid. For example, colloidal particles often carry an electrical charge and therefore attract or repel each other. The charge of both the continuous and the dispersed phase, as well as the mobility of the phases are factors affecting this interaction.

Typically, the ratio the number of molecules of the component (i) to the component (ii) in the anti-microbial compositions ranges from about 100:1 to 5:1, preferably from about 90:1 to about 8:1, more preferably from about 80:1 to about 15:1, still more preferably from about 70:1 to about 25:1 or about 20:1, most preferably from about 40:1 to about 60:1, for example about 50:1.

The ratio of molecules of the component (i) to molecules of the optional additional anti-microbial agent, if used, is typically from about 1:2 or about 1:1 to about 50:1, preferably about 2:1 to about 30:1, more preferably from about 4:1 to about 20:1, most preferably from about 8:1 to about 15:1, for example about 10:1.

In a typical composition the total number of molecules of (i) and (iv) to every molecule of (ii) is from about 5 to about 80, for example from about 10 to about 60, e.g. around 50.

Typically, component (i) is present in the compositions in an amount of from about 0.01 to about 50% by weight of the compositions, such as from about 0.02 to about 40%, for example from about 0.05 to about 30%, preferably from about 0.1 to about 20% (e.g. from 0.2 to 15% or 0.5 to 10%).

Typically, the component (ii) is present in the compositions in an amount of from about 0.001 to about 10% by weight of the compositions, such as from about 0.002 to about 5%, for example from about 0.003 to about 2%, preferably from about 0.005 to about 1% (e.g. from 0.008 to 0.8% or 0.1 to 0.5%). The amount of component (ii) will vary depending on a number of factors, the colloid-forming material used and its properties (e.g. viscosity and volatility).

Typically, the polar solvent component (iii) is present in the compositions in an amount of from about 10 to about 99.999% by weight of the compositions, such as from about 50 to about 99.999%, for example from about 80 to about 99.99%, preferably from about 90 to about 99.9%, more preferably from about 95 to about 99.8% (e.g. from 97 to 99.7% or 97.5 to 99.6%).

Typically, the additional anti-microbial agent(s), such as PHMB, is present in the compositions in an amount of from about 0.001 to about 10% by weight of the compositions, such as from about 0.005 to about 5%, for example from about 0.01 to about 2%, preferably from about 0.05 to about 1% (e.g. from 0.1 to 0.5%).

We use the term colloid herein to encompass various colloidal structures including but not limited to vesicles and micelles, which may for example by spherical or cylindrical.

Anti-microbial compositions which are suitable for use in the present invention include but are not limited to those described in WO2002/62142, GB-A-2374011 and in GB patent application no. PCT/GB2008/002436.

The formulations of the present invention typically comprise an anti-microbial composition as described above in combination with compatible ingredients which allow the formulation to perform its primary purpose. By this we mean for example that a detergent formulation of the invention (such as a washing up liquid) would contain ingredients to provide the necessary cleaning properties together with an anti-microbial composition as described above.

The following are non-limiting examples of formulations of the invention:

A formulation comprising:

(A) at least one non-ionic surfactant;
(B) an anti-microbial composition comprising (i) at least one quaternary ammonium compound, (ii) at least one siloxane or polysiloxane, (iii) at least one polar solvent, typically water, and (iv) at least one additional anti-microbial agent, for example a polymeric biguanidine, such as PHMB; and Other compatible ingredients as described above.

(A) may, for example, comprise one or more non-ionic surfactants only, ie the formulation does not comprise other surfactants such as amphoteric surfactants. The polymeric biguanidine may, for example, be the only additional anti-microbial. In one aspect, the additional anti-microbial agent does not comprise an isothiazalone.

A formulation comprising:

(A) at least one non-ionic surfactant and at least one amphoteric surfactant provided that the total amount of amphoteric surfactant 5% by weight or less based on the total weight of the formulation;
(B) an anti-microbial composition comprising (i) at least one quaternary ammonium compound, (ii) at least one siloxane or polysiloxane, (iii) at least one polar solvent, typically water, and (iv) at least one additional anti-microbial agent, for example a polymeric biguanidine such as PHMB; and Other compatible ingredients as described above.

The polymeric biguanidine may, for example, be the only additional anti-microbial. In one aspect, the additional anti-microbial agent does not comprise an isothiazalone.

A formulation having a pH of about 8 or less, such as from about 5 to about 8 and comprising:

(A) at least one surfactant which exhibits non-ionic or cationic type properties at a pH below about 8;
(B) an anti-microbial composition comprising (i) at least one quaternary ammonium compound, (ii) at least one siloxane or polysiloxane, (iii) at least one polar solvent, typically water, and (iv) at least one additional anti-microbial agent, for example a polymeric biguanidine, such as PHMB; and Other compatible ingredients as described above.

(A) may, for example, comprise one or more non-ionic surfactants only, ie the formulation does not comprise other surfactants such as amphoteric surfactants. The polymeric biguanidine may, for example, be the only additional anti-microbial. In one aspect, the additional anti-microbial agent does not comprise an isothiazalone.

The formulations of the present invention can be made by introducing an amount of an anti-microbial composition as described above into a pre-prepared initial formulation. For example, an anti-microbial composition could be introduced into a suitable commercially available detergent composition. Alternatively, the anti-microbial composition may be incorporated into a formulation by addition during one of the steps in the process for making the formulation (ie without the formation of an initial formulation).

The method that is used to make a particular formulation of the invention may depend on the nature of the formulation and the conditions under which it is made. However, regardless of the method by which the formulation is made it is essential that the anti-microbial composition is pre-formed before it is mixed with any of the other components of the formulation.

Without wishing to be bound by theory, it is believed that the colloidal structure of the anti-microbial composition is maintained in the formulation.

This retention of the structure of the anti-microbial composition can provide one or more of the following advantages.

In use, the formulations of the invention act to substantially reduce or control the formation of microbial colonies on or at the surface to which they are applied. This means that not only do the formulations of the invention kill any microorganisms that are present on a surface when they are applied to that surface (so called "wet kill"), they also have a residual effect in that they prevent the formation of new microbial colonies at the surface (so called "dry kill"). It is believed that the colloids present in the anti-microbial compositions remain on the surface even after the rest of the formulation has been removed and that the presence of the colloids on the surface prevents bio-film formation/the growth of colonies of microorganisms.

The formulations of the invention can have increased anti-microbial efficiency in use compared to formulations which contains the same quantity of anti-microbial agent where that anti-microbial agent is not included within an anti-microbial composition as described above. This is particularly surprising because the surfactants used in anti-microbial compositions used in the invention do not themselves have any anti-microbial properties. This means that the amount of anti-microbial agent required in the formulations of the invention to give the desired effect can be lower than might otherwise be required.

The formulations of the invention may also have one or more of the following advantages:

It is believed that the anti-microbial effect of the present invention is achieved because the anti-microbial composition physically disrupts the adhesion and attachment of a microorganism to a surface, which is a feature that is common to a wide range of microorganisms, including bacteria, fungi and moulds, the compositions are effective against a broad range of microorganisms. Thus, an advantage of the invention is that it is possible to prevent a broad range of microorganisms from adhering and attaching to the surface, and, therefore, from forming a biofilm. Large numerous colonies are also substantially prevented from forming. Thus, the ability of the colony to grow is substantially reduced or even prevented. The invention is therefore general in its control of microorganisms.

Typically, the formulations of the invention do not need to contain materials that are highly toxic to mammals. The anti-microbial agents used in the anti-microbial compositions are typically well known and widely understood and tested anti-microbial agents. The efficacy of the known anti-microbial agents is amplified in the formulations of the invention. Therefore, anti-microbial agents that have a low toxicity can be used in the anti-microbial compositions. In contrast, many "new" anti-microbial agents for known techniques of sanitization use "stronger", more toxic and/or little tested materials.

The anti-microbial compositions used in the invention do not introduce into the formulations of the invention materials that produce highly persistent residues or rinsates or products that contain heavy metals and their salts. Thus, there is a greatly reduced risk of long term hazards.

The anti-microbial compositions used in the invention do not interfere with the biochemical reproductive pathways of the micro-organisms they control. The risk of resistance build up and the development of resistant strains is, therefore, low.

It is believed that in many uses the anti-microbial compositions used in the formulations of the invention provide a pseudo-mordant effect similar to that used to "fix" dye stuffs. The component (ii) of the anti-microbial compositions is insoluble in water and often has a strong affinity to surfaces which are treated with the formulations of the invention. For example, the component (ii) has a strong affinity to textile fibres. Thus in, for example, a laundry process such as machine washing, the hydrophobic component (ii) is attracted to and binds (non-chemically) with fibres. As described above, in the formulations of the invention component (ii) is present in the form of colloidal structures containing the anti-microbial agent(s) and component (ii). Thus, when component (ii) binds to a surface such as a textile surface it has the effect of binding the anti-microbial agent(s) to the surface. They therefore remain on the surface and provide anti-microbial properties even after washing and drying.

The use of at least one non-ionic surfactant in the formulations of the invention can in some instances enhance the anti-microbial properties of the formulations.

As general rule, the antimicrobial efficacy increases with increasing concentration of the antimicrobial agents. However, the formulations of the invention can be surprisingly effective even in environments in which they are significantly diluted such as during laundry processes and household cleaning processes.

The formulations of the invention can be effective when the total concentration of the anti-microbial agents (i) is as low as from about 300 to about 40 ppm or about 50 ppm for example about 200 to about 75 ppm, or about 150 to about 100 ppm. This is very surprising as it is thought that in conventional anti-microbial compositions (such as those comprising quaternary ammonium compounds) the concentration of anti-microbial agent must be at least about 400 ppm. In other words, the formulations of the invention are effective to provide an anti-microbial effect against the level/concentration of micro-organisms found in the environments/conditions in which the formulations of the invention are intended to be used.

The anti-microbial compositions used in the formulations of the invention can have a duel effect in that not only do they provide an anti-microbial effect in use but they can also have a preservative effect on the formulation. This means that it is typically not necessary to include additional preservatives in the formulations of the invention and/or the shelf life of the formulations can be improved.

The use of the shorter chain siloxanes within the definition of component (ii) used above can provide other particular additional advantages. For example, if the colloid is broken (e.g. on a surface due to abrasion) these relatively volatile materials evaporate so that they do not persist on the surface.

The colloids do not typically give surfaces to which they are applied a greasy feel.

The anti-microbial compositions used in the invention can provide the formulations with a very good hand feel, which is important in formulations for personal care such as bath and shower products, soaps and hand sanitizing etc.

Products for use on the skin can provide anti-fungal, anti-microbial, odour prevention, reduced risk of infection and/or enhanced healing benefits. For example, baby products such as nappy cream can reduce the occurrence of conditions such as nappy rash.

Hair care products of the invention can be used to prevent/reduce scalp odour and/or reduce the ability of head lice eggs to attach to the hair.

Food sprays can reduce/prevent spoilages of food by preventing microbial build up.

According to a further aspect of the invention, there is provided the use of formulation of the invention to prevent the formation of colonies of micro-organisms on a surface at which it is provided.

The invention will now be illustrated by the following non-limiting Examples.

The following ingredients were used in the Examples described below.

3 cSt(Byot)Silicone (from Clearco Products Co., Inc, PA, USA)

| Ingredient | CAS Number | Percentage |
|---|---|---|
| Polydimethylsiloxanes | 63148-62-9 | >80 |
| Dodecamethylpentasiloxanes | 141-63-9 | <20 |
| Decamethyltetrasiloxane | 141-62-8 | <5 |
| Octamethylcyclotetrasiloxane | 556-67-2 | <2 |

Vantocil TG (PHMB), Polyhexamethylene Biguanidine (from Arch Chemicals Ltd, West Yorkshire, UK)

An aqueous solution of PHMB, 20% w/w

Mason Quat MQ624M, (from Mason Chemical Company, Illinois, USA)

| Ingredient | CAS Number | Percentage |
|---|---|---|
| benzyl ammonium chloride | 68424-85-1 | 32 |
| Didecyl dimethyl ammonium chloride | 7173-51-5 | 12 |
| Decyloctyl dimethyl ammonium chloride | | 24 |
| Dioctyl dimethyl ammonium chloride | | 12 |
| Water | 7732-18-5 | 10 |
| Ethanol | 64-17-5 | 10 |

Water

Drinking water

Surfactants

Surfac 65/95, Surfac 65/95 pH 9.5, Surfac 65/95 pH 2.5, Neodol 25-7, Neodol 91-8, Surfac LM 90/85, Surfac T80, Surfac APGI, Surfac PGHC and Nimol 49 CE from Surfachem, Leeds, UK.

Tween 60, Tween 40 and Tween 20 from Aldrich, UK.

Gland 3 from Greylands, Manchester, UK.

Tomadol PF9 from Tomah, USA.

Surfac AO30 from Surfachem (amine oxide)

Surfac B4

The anti-microbial composition that was used in each of the Examples below was made by the following method.

REFERENCE EXAMPLE 1

Preparation of the Anti-microbial Composition G5

Step 1

Mason Quat MQ624M was mixed with 3.85% by weight of 3 cSt(Byotrol) silicone (Clearco) and stirred at room temperature for a minimum of 30 minutes. The resulting mixture was clear and was left a further 12 hours.

Step 2

To 130 g of the product of step 1 was added 500 g of Vantocil TG (UK) or Vantocil P (US) and 370 g of Water. This is stirred at room temperature for 30 minutes to completely dissolve the Vantocil.

These steps produced the anti-microbial composition, G5, which comprised 10% by weight quaternary ammonium compounds, 10% by weight PHMB and 0.5% by weight silicone.

EXAMPLE 1

Evaluation of Bactericidal Activity Using Suspension Tests with *Escherichia coli* K12 O Rough H48

The aim of the test is to evaluate the bactericidal activity of products of the invention against *Escherichia coli* K12 O Rough H48.

Media and Materials

| | | |
|---|---|---|
| Luria broth (LB) | 10 g tryptone + 5 g yeast extract + 10 g NaCl/L water | LB is sterilized by autoclaving. |
| Luria broth Aga (LBA) | 15 g agar + 10 g tryptone + 5 g yeast extract + 10 g NaCl/L water | LBA is sterilized by autoclaving. |
| Neutralising solution (NF) | 30 mL Tween 80 + 30 g saponine + 1 g histidine + 1 g cysteine/L water | NF is sterilized by autoclaving. |
| Luria broth + Neutralising solution (LB + NF) | 10 g tryptone + 5 g yeast extract + 10 g NaCl + 30 mL Tween 80 + 30 g saponine + 1 g histidine + 1 g cysteine/L water | LB + NF is sterilized by autoclaving. |
| Sterile desalted water | | |
| Bovine albumin solution | 3% BSA | Sterilized by means of Millipore filter. Used with other liquids in final concentration of 0.3% BSA |
| Incubator 37° C. | | |
| Stopwatch | | |
| Vortex mixer | | |
| Variable pipette and sterile tips | | |
| 100 mm Petri dishes | | |
| 300 ml Flasks | | |

Test Organisms

*Escherichia coli* K12 O Rough H48

The test organism was kept on LBA plates at 4° C. One colony was used to inoculate a 100 ml Flask of LB and incubated at 37° C. for 16 hours to reach stationary phase. For log phase cultures, 4 ml LB were inoculated with one colony and incubated at 37° C. for 16 hours. 1 ml of the bacterial suspension was then added to 100 ml LB and grown to an $OD_{600}$ of approximately 0.375. Serial dilutions of each organism were then performed using LB and plated onto LBA plates to determine the number of colony forming units per ml.

Validation of Test Conditions

1. Validation of Selected Experimental Conditions 1 ml of Bovine Albumin solution (BSA) was placed in a test tube with 1 ml of bacterial test suspension containing approximately $3.0 \times 10^8$ cfu/ml and incubated at the test temperature of 20° C. for 2 minutes. At the end of this time 8 ml of LB was added. This mixture was incubated for the test contact time of 10 minutes. The solution was then diluted to $3.0 \times 10^3$ and $3.0 \times 10^2$ cfu/ml. 0.1 ml of these test solutions were pipetted in triplicate and plated on 12-15 mls of LBA, which is equivalent to $3.0 \times 10^2$ and $3.0 \times 10^1$ cfu. The plates were incubated at 37° C. for 24 hours.

Test result should be equal to or greater than 0.05 times bacterial suspension

2. Neutraliser Toxicity Validation 9 ml of Neutraliser (NF) was placed in a test tube and mixed with 1 ml of a bacterial suspension containing approximately $3.0 \times 10^8$ cfu/ml. The mixture was incubated at 20° C. for 10 minutes. The suspension was diluted to $3.0 \times 10^3$ and $3.0 \times 10^2$ cfu/ml using LBA. 0.1 ml was then pipetted onto triplicate plates containing 12-15 mls of LBA. The plates were incubated at 37° C. for 24 hours.

Test result should be equal to or greater than 0.05 times bacterial suspension

3. Dilution-Neutralisation Validation 1 ml of Bovine albumin solution (BSA) was placed in a test tube with 1 ml of LB and incubated at 20° C. for 5 minutes. 1 ml was then taken and added to 8 ml Neutraliser (NF). After 5 minutes incubation, 1 ml of the bacterial suspension was added. The mixture was left at 20° C. for 10 minutes. The suspension was diluted to $3.0 \times 10^3$ and $3.0 \times 10^2$ cfu/ml using LB and 0.1 ml was then plated in triplicate onto 12-15 mls of LBA. The plates were incubated at 37° C. for 24 hours.

Test result should be equal to or greater than 0.5 times of Neutraliser Toxicity Validation.

Test Method

The selected conditions for the tests were:
Temperature: 20° C.
Contact Time: 2 min
Interfering Substance: Bovine Albumin Solution (0.3%)

Product test solution: Byotrol product G5 (0.5% (v/v), diluted with drinking water) plus indicated surfactants/surfactant mixtures, pH is adjusted as indicated.

1 ml BSA was added to 1 ml of bacterial test suspension (approximately $3 \times 10^5$ cfu/ml) and incubated at 20° C. for 5 minutes. At the end of this time 8 ml of the product test solution was added. After a contact time of 2 minutes, a 1 ml aliquot was pipetted into 9 ml neutraliser (NF). 1 ml of this mixture was used for serial dilutions (LB+NF): $10^{-1}$, $10^{-2}$, $10^{-3}$, $10^{-4}$, $10^{-5}$, $10^{-6}$ and $10^{-7}$. 1 mL of serial dilutions was plated in duplicate into a petri dish with 12-15 mls of LBA.

Product test solutions comprising 0.5% of the G5 solution made as described in Reference Example 1 and a surfactant as listed in the Table 1 below were tested.

TABLE 1

| SURFACTANT | % (v/v) | SURVIVORS (cfu/mL) |
|---|---|---|
| Water only (control) | — | $8 \times 10^7$ |
| Surfac 65/95 | 5.0 | 0 |
| Surfac 65/95 pH 9.5 | 5.0 | 0 |
| Surfac 65/95 pH 2.5 | 5.0 | 0 |
| Surfac 65/95 + M-Inhib | 5.0 | 0 |
| Neodol 25-7 | 5.0 | 0 |
| Surfac LM 90/85 | 5.0 | 0 |
| Surfac T80 | 5.0 | 0 |
| Tween 60 | 5.0 | 0 |
| Tween 40 | 5.0 | 0 |
| Tween 20 | 5.0 | 0 |
| Surfac APGI | 5.0 | 0 |
| Surfac PGHC | 5.0 | 0 |
| Nimol 49 CE | 5.0 | 0 |
| Gland 3 | 5.0 | 0 |
| Tomadol PF9 | 5.0 | 0 |

Table 1 shows that the combination of G5 and 5% v/v of the surfactants tested had antimicrobial activity.

Product test solutions comprising 0.5% v/v of the G5 solution made as described in Reference Example 1 and the nonionic surfactant Tomadol PF9 in an amount of from 0.1 to 30% v/v were tested and the results are shown below in Table 2.

TABLE 2

| SURFACTANT | % (v/v) | SURVIVORS (cfu/mL) |
|---|---|---|
| Water only (control) | — | $8 \times 10^7$ |
| Tomadol PF9 | 0.1 to 30% | 0 |

Table 2 shows that the combination of G5 and the nonionic surfactant Tomadol had antimicrobial activity at concentrations of surfactant up to 30% v/v.

EXAMPLE 2

Evaluation of Bactericidal Activity of Further Samples Using Suspension Tests with *Escherichia coli* K12 O Rough H48

A test procedure similar to that described above in Example 1 was carried out. Product test solutions comprising 0.5% of the G5 solution made as described in Reference Example 1 and a surfactant as listed in the Table 1 below were tested.

| Surfactant | pH | % Kill rate |
|---|---|---|
| B4 (3%) & APG (7%) | 2.5, 6, 10 | 99.9999 |
| B4 (5%) & APG (5%) | 2.5, 5.2, 10 | 99.9999 |
| B4 (1%) & APG (5%) | 2, 3, 4, 5 | 99.9999 |
| Tomadol (9%) & B4 (1%) | 6.3 | 99.9999 |
| Tomadol (8%) & B4 (2%) | 6.3 | 99.9999 |
| Tomadol (7%) & B4 (3%) | 6.3 | 99.9999 |
| Tomadol (6%) & B4 (4%) | 6.3 | 99.9999 |
| Tomadol (5%) & B4 (5%) | 6.3 | 99.9999 |
| Amine oxide (2%) & APG (1%) | 2.5, 7, 10 | 99.9999 |
| Amine oxide (2%) & APG (2%) | 2.5, 7, 10 | 99.9999 |
| Neodol 91-8 (5%) | 2.5, 7, 10 | 99.9999 |
| Neodol 91-8 (10%) | 2.5, 7, 10 | 99.9999 |
| Tomadol (4%) & Coconut fatty acid (0.3%) | 2, 4, 5.5, 9.5, 10 | 99.9999 |

EXAMPLE 3

Residual Efficacy Testing Using *Escherichia coli* K12 O Rough H48

The aim of the test is to evaluate the residual efficacy of products of the invention against *Escherichia coli* K12 O Rough H48 using typical household conditions.

Media and Materials

| Luria broth (LB) | 10 g tryptone + 5 g yeast extract + 10 g NaCl/L water | LB is sterilized by autoclaving. |
|---|---|---|
| Luria broth Aga (LBA) | 15 g agar + 10 g tryptone + 5 g yeast extract + 10 g NaCl/L water | LBA is sterilized by autoclaving. |
| Neutralising solution (NF) | 30 mL Tween 80 + 30 g saponine + 1 g histidine + 1 g cysteine/L water | NF is sterilized by autoclaving. |
| Luria broth + Neutralising solution (LB + NF) | 10 g tryptone + 5 g yeast extract + 10 g NaCl + 30 mL Tween 80 + | LB + NF is sterilized by autoclaving. |

-continued

| | | |
|---|---|---|
| Sterile desalted water | 30 g saponine +<br>1 g histidine +<br>1 g cysteine/L water | |
| Bovine albumin solution | 3% BSA | Sterilized by means of Millipore filter. Used with other liquids in final concentration of 0.3% BSA |

Incubator 37° C.
Stopwatch
Ceramic tiles, glazed (10 cm × 10 cm)
Professional Care Wipes, viskose free
Drigalsky spatula
Vortex mixer
Variable pipette and sterile tips
100 mm Petri dishes
300 ml Flasks Test Organisms

*Escherichia coli* K12 O Rough H48

The test organism was kept on LBA plates at 4° C. One colony was used to inoculate a 100 ml Flask of LB and incubated at 37° C. for 16 hours to reach stationary phase. For log phase cultures, 4 ml LB were inoculated with one colony and incubated at 37° C. for 16 hours. 1 ml of the bacterial suspension was then added to 100 ml LB and grown to an $OD_{600}$ of approximately 0.375. Serial dilutions of each organism were then performed using LB and plated onto LBA plates to determine the number of colony forming units per ml.

Validation of Test Conditions

1. Validation of Selected Experimental Conditions 1 ml of Bovine Albumin solution (BSA) was placed in a test tube with 1 ml of bacterial test suspension containing approximately $3.0 \times 10^8$ cfu/ml and incubated at the test temperature of 20° C. for 2 minutes. At the end of this time 8 ml of LB was added. This mixture was incubated for the test contact time of 10 minutes. The solution was then diluted to $3.0 \times 10^3$ and $3.0 \times 10^2$ cfu/ml. 0.1 ml of these test solutions were pipetted in triplicate and plated on 12-15 mls of LBA, which is equivalent to $3.0 \times 10^2$ and $3.0 \times 10^1$ cfu. The plates were incubated at 37° C. for 24 hours.

Test result should be equal to or greater than 0.05 times bacterial suspension.

2. Neutraliser Toxicity Validation 9 ml of Neutraliser (NF) was placed in a test tube and mixed with 1 ml of a bacterial suspension containing approximately $3.0 \times 10^8$ cfu/ml. The mixture was incubated at 20° C. for 10 minutes. The suspension was diluted to $3.0 \times 10^3$ and $3.0 \times 10^2$ cfu/ml using LBA. 0.1 ml was then pipetted onto triplicate plates containing 12-15 mls of LBA. The plates were incubated at 37° C. for 24 hours.

Test result should be equal to or greater than 0.05 times bacterial suspension

3. Dilution-Neutralisation Validation 1 ml of Bovine albumin solution (BSA) was placed in a test tube with 1 ml of LB and incubated at 20° C. for 5 minutes. 1 ml was then taken and added to 8 ml Neutraliser (NF). After 5 minutes incubation, 1 ml of the bacterial suspension was added. The mixture was left at 20° C. for 10 minutes. The suspension was diluted to $3.0 \times 10^3$ and $3.0 \times 10^2$ cfu/ml using LB and 0.1 ml was then plated in triplicate onto 12-15 mls of LBA. The plates were incubated at 37° C. for 24 hours.

Test result should be equal to or greater than 0.5 times of Neutraliser Toxicity Validation.

Test Method

1. Pretreatment of Carrier

Carriers were cleaned/disinfected with isopropanol (70% v/v) by spraying. Excess isopropanol was used to cover the entire surface completely. Excess isopropanol was removed by running off. Further drying was allowed for a period of 10 minutes.

2. $1^{st}$ Inoculation of Carrier $1^{st}$ challenge of tile surface with ~$10^6$ CFU bacteria. Application volume is set at 10 μL. The applied volume of 10 μL was spread over entire tile surface by means of sterile plastic spatula (Drigalsky spatula). Challenged tile is allowed to dry over a period of 50 minutes.

3. Product Application to Carrier 1 mL of disinfecting product was applied to a pretreated carrier surface. Applied disinfecting product was spread over entire surface by means of sterile plastic spatula (Drigalsky spatula). Surface treatment with excess disinfecting product was done over a period of 10 minutes. Pretreated carriers were stored overnight in a clean place, covered with Professional Care Wipes.

4. Inoculation of Carrier

Inoculation of tile surface was done by using ~$10^6$ CFU bacteria. Application volume was set at 10 μL. If residual amounts of isopropanol remain some of applied bacteria might be killed. The applied volume of 10 μL was spread over entire tile surface by means of sterile plastic spatula (Drigalsky spatula). Challenged tile was allowed to dry over a period of 50 minutes.

5. Rinsing with Water

Tile surface was rinsed with 10 mL sterile water (water$_{millipored}$). After rinsing tile was dried for up to 1 hr or till surface was visibly dry.

6. Dry Wear Cycle

Wear cycles are used as an abrasive step. A dry wear cycle was done by moving a cork block wrapped with Professional Care Wipe back and forth. Normal hand pressure is applied. Professional Care Wipes of non viscose type, do not adsorb quats or PHMB.

7. Wet Wear Cycle

Wetting of Professional Care Wipes was done by spraying water$_{millipored}$ onto wipes. Spraying was done by triggering one time from about 30 cm. Wet wear cycles were used as an abrasive step. A Wet wear cycle was done by moving a cork block wrapped with wetted (water$_{millipored}$) Professional Care Wipe back and forth. Normal hand pressure was applied. The wetted surface was allowed to dry for at least 10 minutes.

8. Final Inoculation of Carrier

The tile is challenged with ~$10^6$ CFU bacteria. The application volume was set at 10 μL. The applied volume was spread over entire tile surface by means of sterile plastic spatula (Drigalsky spatula). The challenged tile was allowed to dry over a period of 5 to 10 minutes. Surviving bacteria were dissolved by applying 500 μL LB+NF. The applied LB+NF was spread over entire tile surface by means of sterile plastic spatula (Drigalsky spatula, single use version). The neutralizer had no killing effect on surviving bacteria, but inactivates the disinfecting product on tiles. To dissolve surviving bacteria the tile was incubated at room temperature for 30 minutes. Dissolved surviving bacteria were collected by means of sterile plastic spatula (Drigalsky spatula).

9. Determination of Survivors

The collected liquid was sampled by means of a sterile pipette. 100 μL of sample was applied to 900 μL of LB+NF. Serial dilution in LB+NF up to $10^{-4}$. 100 μL of sample was carried out and the dilutions are transferred to agar plates.

| Test Method - Total Procedure | | |
|---|---|---|
| # | DAY | PROCEDURE |
| 1 | 1 | Preparation of bacteria culture (overnight culture) |
| 2 | 2 | Pretreatment of carrier (tiles); see Step 1 |
| 3 | | 1$^{st}$ Inoculation of Carrier; see Step 2 |
| 4 | | Product Application to Carrier; see Step 3 |
| 5 | 3 | Wet wear cycle; see Step 7 |
| 6 | | Dry wear cycelde; see Step 6 |
| 7 | | Rinsing with water$_{millipored}$; see Step 5 |
| 8 | 4 | Inoculation of carrier; see Step 4 |
| 9 | | Dry wear cycle; see Step 6 |
| 10 | | Final inoculation of carrier; see Step 8 |
| 11 | 5 | Determination of survivors; see Step 10 |

Test Results

The aqueous formulations that were tested using the procedure described above a shown in Table 3 below.

TABLE 3

| Anti-microbial component | SURFACTANT | % (v/v) of Surfactant | LOG Reduction |
|---|---|---|---|
| none | none | — | 0 |
| G5 0.5% | none | — | 3.5 |
| none | Tomadol PF/9 | 0.5 | 2.8 |
| | | 2.5 | 2.5 |
| | | 5 | 1.5 |
| | | 10 | 1 |
| G5 0.5% | Tomadol PF/9 | 0.5 | 7 |
| | | 2.5 | 7 |
| | | 5 | 7 |
| | | 10 | 7 |
| | Surfac 65/75 | 5 | 7 |

When water alone was used no residual efficacy was observed (shown as log reduction). G5 alone gave a log reduction of 3.5. The surfactants alone had no residual efficacy (Log reduction <3 is within the limits of experimental error). G5 in combination with the surfactants showed pronounced residual efficacy (log reduction of 7).

The invention claimed is:

1. A method of substantially reducing or controlling the formation of microbial colonies on or at a hard surface or skin and providing a residual reduction or controlling effect on or at the hard surface or skin, which method comprises applying to that hard surface or skin a formulation comprising:
   (A) a surfactant component comprising at least one non-ionic surfactant; and
   (B) an anti-microbial composition that comprises (i) an anti-microbial agent with surfactant properties which is at least one quaternary ammonium compound having the formula $(CH_3)_n(A)_mN^+X^-$,
   wherein each A represents, independently, a substituted or unsubstituted and/or straight chain or branched and/or interrupted or uninterrupted alkyl, aryl, alkylaryl, arylalkyl, cycloalkyl, heterocyclyl or alkenyl group or two or more of A together represent a substituted or unsubstituted heterocyclic ring, formed together with the nitrogen atom, and wherein the total number of carbon atoms in the groups A and $CH_3$ is at least 4;
   wherein the substituents for the groups A are selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —O(CR'R")$_r$NC(=O)R', —O(CR'R")$_r$NR"C(=O)R', —O(CR'R")$_r$NR"SO$_2$R', —OC(=O)NR'R", —NR'C(=O)OR", —SO$_2$R', —SO$_2$NR'R", and —NR'SO$_2$R";
   wherein R' and R" are individually hydrogen, $C_1$-$C_8$ alkyl, cycloalkyl, heterocyclyl, aryl, or arylalkyl, and r is an integer from 1 to 6, or R' and R" together form a cyclic functionality;
   wherein the term substituted as applied to alkyl, alkenyl, heterocyclyl, cycloalkyl, aryl, alkylaryl and arylalkyl refers to the substituents described above, starting with F and ending with —NR'SO$_2$R";
   wherein X' is halide or sulphonate;
   wherein n is from 1 to 3 and m is from 1 to 3 provided that the sum of n and m is 4; and
   wherein if each A is an unsubstituted or uninterrupted alkyl, each A is independently a $C_{6-12}$ alkyl group; and
   (ii) a hydrophobic material which comprises at least one siloxane selected from those having the formula $(H_3C)[SiO(CH_3)_2]_nSi(CH_3)_3$, and $(H_3C)[SiO(CH_3)H]_nSi(CH_3)_3$ wherein n is from 1 to 24; and (iii) a polar solvent;
   wherein the formulation does not comprise an anionic surfactant, and the ratio of molecules of component (i) to component (ii) is from 100:1 to 5:1.

2. A method according to claim 1, wherein component (A) comprises at least one amphoteric surfactant.

3. A method according to claim 1 wherein component (A) consists essentially of at least one non-ionic surfactant.

4. A method according to claim 1, wherein the composition (B) comprises an additional anti-microbial agent (iv).

5. A method according to claim 1, wherein the composition (B) comprises colloids which are made up of components (i), (ii) and optionally an additional anti-microbial agent (iv).

6. A method according to claim 1, wherein n=2 and m=2 and each A is a straight chain, unsubstituted and uninterrupted $C_{8-12}$ alkyl group or a benzyl group.

7. A method according to claim 1, wherein the quaternary ammonium compound is a benzalkonium halide or an aryl ring substituted derivative thereof.

8. A method according to claim 7, wherein the benzalkonium halide has the formula:

$$\left[ \text{benzyl-N}^+(\text{CH}_3)_2\text{R} \right] \text{Cl}^-,$$

wherein R is a substituted or unsubstituted and/or straight chain or branched and/or interrupted or uninterrupted alkyl, aryl, alkylaryl, arylalkyl, cycloalkyl, heterocyclyl or alkenyl group.

9. A method according to claim 1, wherein the quaternary ammonium compound is selected from the group consisting of domiphen bromide, benzethonium chloride, benzyldimethyl-n-tetradecyl-ammonium chloride, benzyldimethyl-n-dodecyl-ammonium chloride, n-dodecyl-n-tetradecyldimethyl-ammonium chloride and benzyl-$C_{12}$-$C_{16}$-alkyl-dimethyl-ammonium chloride, benzyl-cocoalkyl-dimethyl-ammonium chloride, di-n-decyldimethylammonium chloride, Maquat A and mixtures thereof.

10. A method according to claim 1, wherein the ratio of molecules of component (i) to component (ii) is from about 40:1 to about 60:1.

11. A method according to claim 1 wherein the siloxane comprises at least one of hexamethyl disiloxane, octamethyl trisiloxane, decamethyl tetrasiloxane and dodecamethyl pentasiloxane.

12. A method according to claim 1, wherein the polar solvent is selected from the group consisting of water, ethanol, n-propanol, ispropanol, diethylene glycol and dipropylene glycol and mixtures thereof.

13. A method according to claim 4, wherein the least one additional anti-microbial agent (iv) is selected from the group consisting of polymeric biguanidines, isothiazalones, ortho phenyl phenol and nitro bromopropanes.

14. A method according to claim 13, wherein the additional anti-microbial agent is polyhexamethylene biguanidine.

15. A method according to claim 4, wherein the total number of molecules of the anti-microbial component (i) and component (iv) to every molecule of component (ii) is from about 5 to about 80.

16. A method according to claim 2 wherein the formulation comprises at least one non-ionic surfactant and at least one amphoteric surfactant, provided that the total amount of amphoteric surfactant is 5% or less based on the total weight of the formulation.

17. A method according to claim 1, wherein the formulation used is in the form of a surface cleaner, a toilet care product, a dishwashing product, an outdoor cleaning product, a personal care product, a baby product, a first aid product, a foot hygiene product or a car cleaning product.

18. A method according to claim 1, wherein the non-ionic surfactant is selected from the group consisting of ethylene oxide/propylene oxide block polymers, polyethoxylated sorbitan esters, fatty esters of sorbitan, ethoxylated fatty esters (containing from 1 to 25 units of ethylene oxide), polyethoxylated $C_8$-$C_{22}$ alcohols (containing from 1 to 25 units of ethylene oxide), polyethyoxylated $C_6$-$C_{22}$ alkylphenols (containing from 5 to 25 units of ethylene oxide), and alkylpolyglycosides.

19. A method according to claim 18, wherein the non-ionic surfactant is a polyethoxylated $C_8$-$C_{22}$ alcohol containing from 1 to 25 units of ethylene oxide.

20. A method according to claim 1, wherein the formulation comprising:
(A) at least one non-ionic surfactant; and
(B) an anti-microbial composition that comprises (i) at least one quaternary ammonium compound as defined in claim 1, (ii) at least one siloxane, including a siloxane as defined in claim 1, (iii) water, and (iv) polyhexamethylene biguanide.

21. A method according to claim 1, wherein the formulation does not contain an isothiazalone.

22. A method according to claim 1, wherein the formulation comprises octyl decyl dimethyl ammonium chloride, didecyl dimethyl ammonium chloride, dioctyl dimethyl ammonium chloride and alkyl dimethyl benzyl ammonium chloride.

23. A method of preventing microorganisms from adhering or attaching to a hard surface or skin or reducing the number of microorganisms that adhere or attach to a hard surface, or a skin and providing residual prevention or reduction to the hard surface or skin, which method comprises applying to that hard surface or skin an anti-microbial formulation comprising:
(A) a surfactant component comprising at least one non-ionic surfactant; and
(B) an anti-microbial composition that comprises (i) an anti-microbial agent with surfactant properties which is at least one quaternary ammonium compound having the formula $(CH_3)_n(A)_mN^+X^-$,
wherein each A represents, independently, a substituted or unsubstituted and/or straight chain or branched and/or interrupted or uninterrupted alkyl, aryl, alkylaryl, arylalkyl, cycloalkyl, heterocyclyl or alkenyl group or two or more of A together represent a substituted or unsubstituted heterocyclic ring, formed together with the nitrogen atom, and wherein the total number of carbon atoms in the groups A and $CH_3$ is at least 4;
wherein the substituents for the groups A are selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, —OR', —NR'R", —$CF_3$, —CN, —$NO_2$, —$C_2R'$, —SR', —$N_3$, —C(=O)NR'R", —NR'C(=O)R", —C(=O)R', —C(=O)OR', —OC(=O)R', —O(CR'R")$_r$NC(=O)R', —O(CR'R")$_r$NR"C(=O)R', —O(CR'R")$_r$NR"$SO_2R'$, —OC(=O)NR'R", —NR'C(=O)OR", —$SO_2R'$, —$SO_2NR'R"$, and —NR'$SO_2R"$;
wherein R' and R" are individually hydrogen, $C_1$-$C_8$ alkyl, cycloalkyl, heterocyclyl, aryl, or arylalkyl, and r is an integer from 1 to 6, or R' and R" together form a cyclic functionality;
wherein the term "substituted" as applied to alkyl, alkenyl, heterocyclyl, cycloalkyl, aryl, alkylaryl and arylalkyl refers to the substituents described above, starting with F and ending with —NR'$SO_2R"$;
wherein X' is halide or sulphonate;
n is from 1 to 3 and m is from 1 to 3 provided that the sum of n and m is 4; and
wherein if each A is an unsubstituted or uninterrupted alkyl, each A is independently a $C_6$-$_{12}$ alkyl group; and
(ii) a hydrophobic material which comprises at least one siloxane selected from those having the formula $(H_3C)$[SiO$(CH_3)_2$]$_n$Si$(CH_3)_3$, and $(H_3C)$[SiO$(CH_3)$H]$_n$Si$(CH_3)_3$ wherein n is from 1 to 24; and (iii) a polar solvent;
wherein the formulation does not comprise an anionic surfactant, and the ratio of molecules of component (i) to component (ii) is from 100:1 to 5:1.

24. A method according to claim 1, which is a first aid method.

25. A method according to claim 23, which is a first aid method.

* * * * *